US011278220B2

(12) United States Patent
Tucker et al.

(10) Patent No.: US 11,278,220 B2
(45) Date of Patent: Mar. 22, 2022

(54) DETERMINING PERIPHERAL OXYGEN SATURATION (SPO2) AND HEMOGLOBIN CONCENTRATION USING MULTI-SPECTRAL LASER IMAGING (MSLI) METHODS AND SYSTEMS

(71) Applicant: East Carolina University, Greenville, NC (US)

(72) Inventors: Bryent Tucker, Rocky Mount, NC (US); T. Bruce Ferguson, Jr., Raleigh, NC (US); Cheng Chen, Greenville, NC (US)

(73) Assignee: East Carolina University, Greenville, NC (US)

( * ) Notice: Subject to any disclaimer, the term of this patent is extended or adjusted under 35 U.S.C. 154(b) by 0 days.

(21) Appl. No.: 16/433,716

(22) Filed: Jun. 6, 2019

(65) Prior Publication Data

US 2019/0374140 A1  Dec. 12, 2019

Related U.S. Application Data

(60) Provisional application No. 62/682,219, filed on Jun. 8, 2018.

(51) Int. Cl.
*A61B 5/00* (2006.01)
*A61B 5/1455* (2006.01)
(Continued)

(52) U.S. Cl.
CPC ........ *A61B 5/14552* (2013.01); *A61B 5/0075* (2013.01); *A61B 5/0077* (2013.01);
(Continued)

(58) Field of Classification Search
CPC . G01J 3/00; G01J 3/2823; G01J 3/427; A61B 5/0075; A61B 5/0077; A61B 5/0082; A61B 5/026; A61B 5/0261
See application file for complete search history.

(56) References Cited

U.S. PATENT DOCUMENTS 8,644,911 B1 * 2/2014 Panasyuk ............. A61B 5/0075
600/473
9,226,673 B2  1/2016 Ferguson, Jr. et al.
(Continued)

FOREIGN PATENT DOCUMENTS

CA         2658811 A1       2/2007
WO   WO 2007/136880 A2    11/2007
WO   WO 2016/153741 A1     9/2016

OTHER PUBLICATIONS

Notification of Transmittal of the International Search Report and the Written Opinion of the International Searching Authority, or the Declaration, PCT/US2019/035792, dated Sep. 10, 2019, 11 pages.
(Continued)

*Primary Examiner* — Jonathan M Hansen
(74) *Attorney, Agent, or Firm* — Stanek Lemon Crouse & Meeks, PA

(57) ABSTRACT

Some embodiments of the present inventive concept provide a multispectral imaging system including a first light source, the first light source having a first wavelength configured to produce a non-coherent illumination to image a sample; a second coherent light source, different from the first light source, having a second wavelength, different from the first wavelength, configured to image the sample simultaneously with the first light source; a camera configured to simultaneously receive information related to the first and second light sources from the sample, wherein light at the first wavelength is configured to image a surface of the sample into the camera and light at the second wavelength is configured to penetrate the sample and provide information related to the penetrated sample to the camera; and a processor configured to combine the received information related to the first and second light sources and generate a synthesized image of the anatomical structure and the physi-
(Continued)

ology of blood flow and perfusion of the sample in terms of blood flow rate distribution.

19 Claims, 22 Drawing Sheets

(51) Int. Cl.
  *G06T 7/00* (2017.01)
  *A61B 5/026* (2006.01)
(52) U.S. Cl.
  CPC .......... *G06T 7/0012* (2013.01); *A61B 5/0066* (2013.01); *A61B 5/0261* (2013.01); *A61B 5/441* (2013.01); *A61B 5/7203* (2013.01); *G06T 2207/10024* (2013.01); *G06T 2207/30004* (2013.01)

(56) References Cited

U.S. PATENT DOCUMENTS

| | | | |
|---|---|---|---|
| 9,271,658 | B2 | 3/2016 | Ferguson, Jr. et al. |
| 9,480,424 | B2 | 11/2016 | Darty et al. |
| 10,058,256 | B2* | 8/2018 | Chen ................... A61B 5/0261 |
| 10,205,892 | B2 | 2/2019 | Darty |
| 10,390,718 | B2* | 8/2019 | Chen ................... A61B 5/721 |
| 2003/0158470 | A1 | 8/2003 | Wolters |
| 2011/0090325 | A1 | 4/2011 | Hauger et al. |
| 2012/0277559 | A1 | 11/2012 | Kohl-Bareis |
| 2013/0012794 | A1 | 1/2013 | Zeng |
| 2015/0078642 | A1 | 3/2015 | Fang |
| 2015/0282749 | A1 | 10/2015 | Zand et al. |
| 2016/0022181 | A1 | 1/2016 | Valsan et al. |
| 2016/0345835 | A1 | 12/2016 | Darty |
| 2017/0198349 | A1 | 7/2017 | Rice |
| 2017/0236281 | A1* | 8/2017 | Dacosta ................ G06T 7/0016 382/128 |
| 2017/0274205 | A1 | 9/2017 | Chen et al. |
| 2017/0278238 | A1 | 9/2017 | Noji |
| 2018/0092699 | A1 | 4/2018 | Finley |
| 2018/0153422 | A1* | 6/2018 | Watanabe .......... A61B 5/02433 |
| 2018/0234603 | A1 | 8/2018 | Moore |
| 2019/0008387 | A1* | 1/2019 | Godavarty ........... A61B 5/0261 |

OTHER PUBLICATIONS

A. A. Kamshilin, M. A. Volynsky, O. Khayrutdinova, D. Nurkhametova, L. Babayan, A. V. Amelin, O. V. Mamontov, and R. Giniatullin, "Novel capsaicin-induced parameters of microcirculation in migraine patients revealed by imaging photoplethysmography," The journal of headache and pain 19, 43 (2018).
A. Jubran, "Pulse oximetry," Critical care 19, 272 (2015).
A. Nouvong, B. Hoogwerf, E. Mohler, B. Davis, A. Tajaddini, and E. Medenilla, "Evaluation of Diabetic Foot Ulcer Healing With Hyperspectral Imaging of Oxyhemoglobin and Deoxyhemoglobin," Diabetes Care 32, 2056-2061 (2009).
Akobeng AK. Understanding diagnostic tests 3: Receiver operating characteristic curves, Acta Paediatr 2007; 96: 644-6screening47.
Alahdab F, Wang AT, Elraiyah TA, Malgor RD, Rizvi AZ, Lane MA, Prokop LJ, Montori VM, Conte MS, Murad MH. A systematic review for the screening for peripheral arterial disease in asymptomatic patients. J Vasc Surg 2015; 61: 42S-53S.
Bornstein JE, Munger JA, Deliz JR, Mui A, Cheng C, Kim S, Khaitov S, Chessin DB, Ferguson TB, Bauer JJ. Assessment of bowel end perfusion after mesenteric division: eye vs: SPY. 2018. J Surg Res 230:179-185.
Briers D DD, Hirst E, Kirkpatrick SJ, Larsson M, Steenbergen W, Stromberg T, Thompson OB. Laser speckle contrast imaging: Theoretical and practical limitations. Journal of biomedical optics 2013; 18: 066018.

C. Chen, J. Q. Lu, K. Li, S. Zhao, R. S. Brock, and X. H. Hu, "Numerical study of reflectance imaging using a parallel Monte Carlo method," Med. Phys. 34, 2939-2948 (2007).
Carreau A, El Hafny-Rahbi B, Matejuk A, Grillon C, Kieda C, Why is the partial oxygen pressure of human tissues a crucial parameter? Small molecules and hypoxia. J Cell Mol Med 2011; 15:1239-1253.
Collins JA, Rudenski A, Gibson J, Howard L, O'Driscoll R. Relating oxygen partial pressure, saturation and content: The haemoglobin-oxyger dissociation curve. Breathe (Sheff) 2015; 11: 194-201.
Criqui MH, Aboyars V. Epidemiology of peripheral artery disease. Circulation research 2015; 116: 1509-1526.
D. Alvarez, R. Hornero, J. V. Marcos, and F. d. Campo, "Multivariate Analysis of Blood Oxygen Saturation Recordings in Obstructive Sleep Apnea Diagnosis," IEEE Transactions on Biomedical Engineering 57, 2816-2824 (2010).
Davies JL CC, Piek JJ. Coronary physiological parameters at a crossroads. EuroIntervention : journal of EuroPCR in collaboration with the Working Group on Interventional Cardiology of the European Society of Cardiology 2017; 13:1-4.
De Bruyne B, Pijls NH, Kalesan B, Barbato E, Tonino PA, Piroth Z, Jagie N, Mobius-Winkler S, Rioufol G, Witt N, Kala P, MacCarthy P, Engstrom T, Oldroyd KG, Mavromatis K, Manoharan G, Verlee P, Frobert O, Curzen N, Johnson JB, Juni P, Fearon WF. Fractional flow reserve-guided pci versus medical therapy in stable coronary disease. N Engl J Med 2012; 367: 991-1001.
Ferguson TB Jr BA. Improving the quality and outcomes of coronary artery bypass grafting procedures. Expert Review of Cardiovascular Therapy 2016; 14: 617-631.
Ferguson TB Jr CC, Kim S, Jacobs K, Zeng Z, Zhu Z, Buch A, Basham J. Noninvasive quantification of blood fow in epicardial coronary arteries, coronary artery bypass grafts, and anastomoses. Innovations 2017; 12: 50-59.
Ferguson TB, Jr., Chen C, Babb JD, Efird JT, Daggubati R, Cahill JM. Fractional flow reserve-guided coronary artery bypass grafting: Can intraoperative physiologic imaging guide decision making? J Thorac Cardiovasc Surg 2013; 146: 824-835 e821.
Force USPST, Curry SJ, Krist AH, Owens DK, Barry MJ, Caughey AB, Davidson KW, Doubeni CA, Epling JW, Jr., Kemper AR, Kubik M, Landefeld CS, Mangione CM, Silverstein M, Simon MA, Tseng CW, Wong JB. Screening for peripheral artery disease and cardiovascular disease risk assessment with the ankle-brachial index: US preventive services task force recommendation statement. JAMA 2018; 320: 177-183.
Fowkes FG MG, Butcher I, et al. Ankle Brachial Index Collaboration. Ankle brachial index combined with framingham risk score to predict cardiovascular events and mortality. JAMA 2008; 300: 197-2008.
Fowkes FGR, Rudan D, Rudan I, Aboyans V, Denenberg JO, McDermott MM, Norman PE, Sampson UKA, Williams LJ, Mensah GA, Criqui MH. Comparison of global estimates of prevalence and risk factors for peripheral artery disease in 2000 and 2010: A systematic review and analysis. The Lancet 2013; 382: 1329-4340.
G. C. Gurtner, G. E. Jones, P.C. Neligan, M. I. Newman, B. T. Phillips, J. M. Sacks, and M. R. Zenn, "Intraoperative laser angiography using the SPY system: review of the literature and recommendations for use," Annals of Surgical Innovation and Research 7, 1 (2013).
Gerhard-Herman MD, Gornik HL, Barrett C, Barshes NR, Corriere MA, Drachman DE, Fleisher LA, Fowkes FG, Hamburg NM, Kinlay S, Lookstein R, Misra S, Mureebe L, Olin JW, Patel RA, Regensteiner JG, Schanzer A, Shishehbor MH, Stewart KJ, TreatJacobson D, Walsh ME. 2016 aha/acc guideline on the management of patients with lower extremity peripheral artery disease: A report of the american college of cardiology/american heart association task force on clinical practice guidelines. Circulation 2017; 135: e726-e779.
Gerhard-Herman MD, Gornik HL, Barrett C, Barshes NR, Corriere MA, Drachman DE, Fleisher LA, Fowkes FG, Hamburg NM, Kinlay S, Lookstein R, Misra S, Mureebe L, Olin JW, Patel RA, Regensteiner JG, Schanzer A, Shishehbor MH, Stewart KJ, TreatJacobson D, Walsh ME. 2016 aha/acc guideline on the management of patients with lower extremity peripheral artery disease: Executive

(56) References Cited

OTHER PUBLICATIONS summary: A report of the american college of cardiology/american heart association task force on clinical practice guidelines. Circulation 2017; 135: e686-e725.

Gomaa D, Rodriquez D, Jr., Petro M, Blakeman TC, Branson RD. Impact of oxygenation status on the noninvasive measurement of hemoglobin. Mil Med 2017; 182: 87-91.

Guirguis-Blake JM, Evans CV, Redmond N, Lin JS. Screening for peripheral artery disease using the ankle-brachial index: Updated evidence report and systematic review for the us preventive services task force. JAMA 2018; 320: 184-196.

Hlatky MA, De Bruyne B, Pontone G, Patel MR, Norgaard BL, Byrne RA, Curzen N, Purcell I, Gutberlet M, Rioufol G, Hink U, Schuchlenz HW, Feuchtner G, Gilard M, Andreini D, Jensen JM, Hadamitzky M, Wilk A, Wang F, Rogers C, Douglas PS, Investigators P. Quality of life and economic outcomes of assessing fractional flow reserve with computed tomography angiography: The platform study. J Am Coll Cardiol 2015, 10.1016/j.jacc.2015.09.051.

J. Allen, "Photoplethysmography and its application in clinical physiological measurement," Physiological Measurement 28, R1-R39 (2007).

J. Q. Lu, C. Chen, D. W. Pravica, R. S. Brook, and X. H. Hu, "Validity of a closed-form diffusion solution in P1 approximation for reflectance imaging with an oblique beam of arbitrary profile," Med. Phys. 35, 3979-3987 (2008).

Jelani QU, Petrov M, Martinez SC, Holmvang L, Al-Shaibi K, Alasnag M. Peripheral arterial disease in women: An overview of risk factor profile, clinical features, and outcomes. Curr Atheroscler Rep 2018; 20: 40.

Khan TH FF, Niazi K. Critical review ofthe ankle brachial index. Current Cardiology Reviews 2008; 4: 101-106.

Kim SK HL, McNames J. Tracking of rhythmical biomedical signals using the maxima a posteriori adaptive marginalized particle filter. British Journal of Health Informatics and Monitoring 2015; 2.

L Higgins G. What is the potential for false positive results in ankle brachial index measurements performed byemergency providers? Journal of General Practice 2013; 01.

Leach RM, Treacher DF. Oxygen transport: 2: Tissue hypoxia. BMJ 1998; 317(7169):1370-1373.

Lijmer JG HM, van den Dungen JJAM, Loonstra J, Smit AJ. Roc analyses of non-invasive tests for peripheral arterial disease. Ultrasound in Med and Biol 1996; 22: 391-398.

Loong T-W. Clinical review: Understanding sensitivity and specificity with the right side of the brain. BMJ 2003; 327: 716-719.

M. R. Future, "Perfusion Imaging Market Research Report—Global Forecast till 2024," (WantStats Research And Media Pvt Ltd, 2019).

MacIntyre NR. Tissue hypoxia: implications for the respiratory clinician. Respiratory Care 2014. 59(10):1590-1596.

Martin DS, Khosravi M, Grocott M, Mythen MG. Concepts in hypoxia reborn. Crit Care 2010; 14(4):315.

McDermott M, Criqul MH. Ankle-brachial index screening and improving peripheral artery disease detection and outcomes. JAMA 2018; 320: 143-145.

McDermott MM. Lower extremity manifestations of peripheral artery disease: The pathophysiologic and functional implications of leg ischemia. Circulation research 2015; 116: 1540-1550.

Michiels C. Physiological and Pathological Responses to Hypoxia. Am J Physiol 2004; 164(6):1875-1882.

P. Tian, C. Chen, J. Jin, H. Hong, J. Q. Lu, and X.-H, Hu, "Quantitative characterization of turbidity by radiative transfer based reflectance imaging," Biomed. Opt. Express 9, 2081-2094 (2018).

P. Tian, X. Chen, J. Jin, J. Q. Lu, X. Liang, and X. H. Hu, "A stochastic model for quantifying effect of surface roughness on light reflection by diffuse reflectance standards," Opt. Eng. 57 (in press) (2018).

Pijls NHJ. Fractional flow reserve to guide coronary revascularization. Circulation Journal 2013; 77: 561-569.

R. Bi, J. Dong, C. L. Poh, and K. Lee, "Optical methods for blood perfusion measurement: theoretical comparison among four different modalities," J. Opt. Soc. Am. A 32, 860-866 (2015).

S. CN, Han SH, Lim SH, Hong YS, Won JH, Bae JI, Jo J. Factors affecting the validity of ankle-brachial index in the diagnosis of peripheral arterial obstructive disease. Angiology 2010; 61: 392-396.

Semenza GL. Vascular Responses to Hypoxia and Ischemia. Arterioscler Thromb Vasc Biol. Apr. 2010: 30(4):648-652.

Thabane L ML, Zhang S, Samaan Z, Marcucci M, Ye C, Thabane M, Giangregoro L, Dennis B, Kosa D, Debono VB, Dillenburg R, Fruci V, Bawor M, Lee J, Wells G, Goldsmith CH. A tutorial on sensitivity analyses in clinical trials: The what, why, when and how. BMC Medical Research Methodology 2013; 13: 1-12.

Tonino PAL dBB, Pijls NHJ, Siebert U, Ikeno F, van't Veer M, Klauss V, Manoharan G, Engstrom T, Oldroyd KG, Ver Lee PN, MacCarthy PA, Fearon WA, for the FAME Study Investigators. Fractional flow reserve versus angiography for guiding percutaneous coronary intervention. N Engl J Med 2009; 360: 213-224.

Vaz PG, Humeau-Heurtier A, Figueiras E, Correia C, Cardoso J. Laser speckle imaging to monitor microvascular blood flow: A review. IEEE Rev Blomed Eng 2016; 9: 106-120.

White CJ. Cookbook medicine is the recipe for successfully managing patients with pad. J Am Coll Cardiol 2018; 72: 1012-1014.

Wikstrom J HT, Johansson L, Lind L, Ahlstrom H. Ankle brachial index < 0.9 underestimates the prevalence of peripheral artery occlusive disease assessed with whole-bodu magnetic resonance angiography in the elderly. Acta Radiologica 2008; 49:143-149.

Wikstrom J, Hansen T, Johansson L, Ahlstrom H, Lind L. Lower extremity artery stenosis distribution in an unselected elderly population and its relation to a reduced ankle-brachial index. J Vasc Surg 2009; 50: 330-334.

X. Chen, Y. Feng, J. Q. Lu, X. Liang, J. Ding, Y. Du, and X. H. Hu, "Fast method for inverse determination of optical parameters from two measured signals," Optics letters 38. 2095-2097 (2013).

Y. An, Y. Kang, J. Lee, C. Ahn, K. Kwon, and C. Choi, "Blood flow characteristics of diabetic patients with complications detected by optical measurement," BioMedical Engineering OnLine 17, 25 (2018).

Y. Sun, and N. Thakor, "Photoplethysmography Revisited: From Contact to Noncontact, From Point to Imaging," IEEE Trans Biomed. Eng. 63, 463-477 (2016).

International Search Report and Written Opinion, PCT/US2019/049489, dated Jun. 3, 2020.

Tian et al., "Quantitative characterization of turbidity by radiative transfer based reflectance imaging," Biomedical Optics Express, vol. 9, No. 5, pp. 2018-2094, Apr. 4, 2018.

Radrich et al., "Quantitative multi-spectral oxygen saturation measurements independent of tissue optical properties," Journal of Biophotonics, pp. 83-99, Jan. 1, 2016.

International Search Report and Written Opinion, PCT/US2020/022295, dated Jun. 30, 2020, 12 pages.

International Search Report, PCT/US2020/024645, dated Sep. 2, 2020, 9 pages.

HyperView™, HyperMed Medical Spectral Imaging, 2017, 5 pages.

* cited by examiner

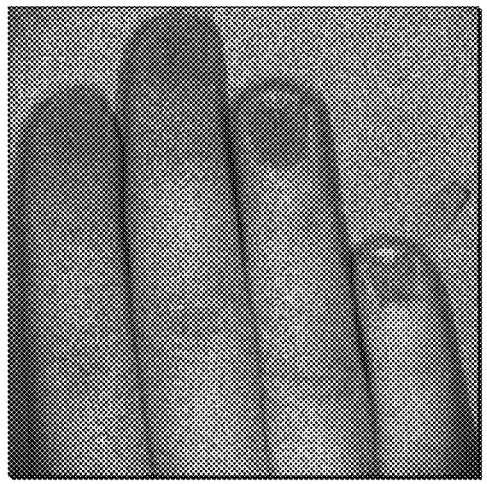 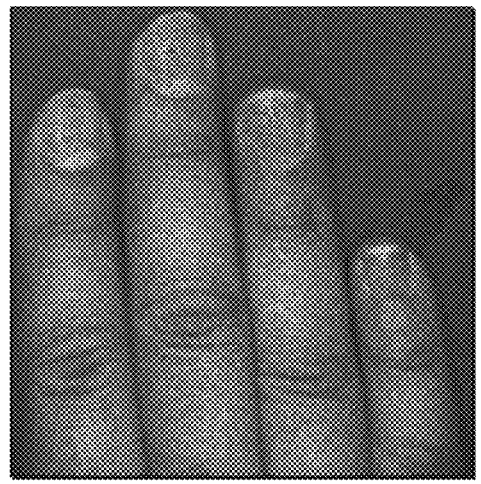 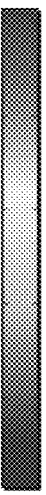
FIG. 7A            FIG. 7B
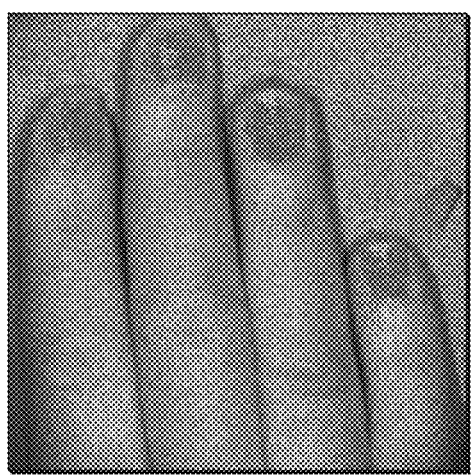 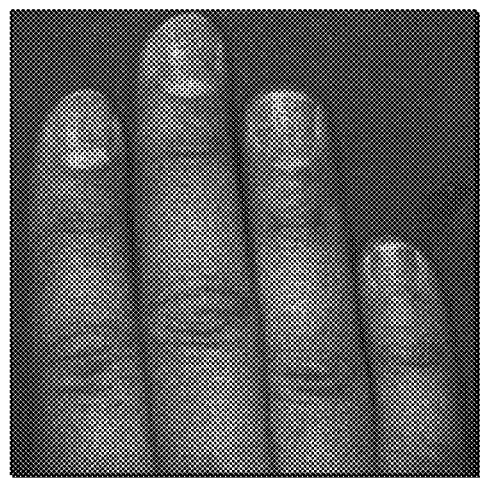 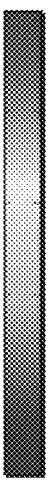
FIG. 8A            FIG. 8B

PANEL A

PANEL B

PANEL A

PANEL B

PANEL C

PANEL D (A+B+C)

HIGH FLOW

MEDIUM FLOW

LOW FLOW

PANEL A

PANEL B

PANEL C (A ADJUSTS BRIGHTNESS AND B ADJUSTS COLOR)

PANEL A

PANEL B

PANEL C

PANEL D

| NAME | WAVELENGTHS | SIZE | PRICE | POWER | PICTURE |
|---|---|---|---|---|---|
| SMD 6 PINS WITH FLAT LENS (MTMD6788594SMT6) | 670nm<br>770nm<br>810nm<br>850nm<br>950nm | 5x5 mm | $40.85 | ~5mW |  |
| TO 5 WITH FLAT LENS (MTMD6891T38) | 670nm<br>850nm<br>950nm<br>1300nm | 9mm | $40.85 | ~3mW |  |
| MODIFIED TO 5 WITH FLAT LENS (MTMD6894T38) | 670nm (2)<br>810nm (2)<br>950nm (2) | 9mm | $30.10 | ~6mW |  |
| TO 18 METAL CAN FLAT LENS (MTE5066W-UR) | 660nm | 5.4mm | $5.88 | ~3mW |  |
| TO 18 METAL CAN FLAT LENS (MTE8800W) | 880nm | 5.4mm | $5.88 | ~4mW |  |

TABLE 1: MARKTECH LED SOURCE OPTIONS

DETERMINING PERIPHERAL OXYGEN SATURATION (SPO2) AND HEMOGLOBIN CONCENTRATION USING MULTI-SPECTRAL LASER IMAGING (MSLI) METHODS AND SYSTEMS

CLAIM OF PRIORITY

The present application claims priority to U.S. Patent Provisional Application Ser. No. 62/682,219, entitled Determining Peripheral Oxygen Saturation ($SpO_2$) and Hemoglobin Concentration using Multi-Spectral laser Imaging (MSLI) Methods and Systems, filed on Jun. 8, 2018, the disclosure of which is hereby incorporated herein by reference as if set forth in its entirety.

FIELD

The present inventive concept relates generally to imaging and, more particularly, to determining peripheral oxygen saturation ($SpO_2$) using imaging techniques, such as Laser Speckle Imaging, Laser Doppler Imaging and the like with multispectral capability.

BACKGROUND

The measurement results of blood flow and perfusion imaging technologies are typically disrupted by a motion artifact of the target tissue/organ in clinical circumstances. This movement can be micro (i.e., pulsatility of an arteriole due to systole and diastole blood pressure levels), intermediate (i.e., normal peristalsis of the small or large bowel) or macro (i.e., the movement of the heart during the cardiac cycle). This movement can be intrinsic to the imaged tissue (i.e., examples cited above), or extrinsic (i.e., the movement of the heart as a result of the movement of the lungs during ventilation). Thus, in many clinical situations, where accurate quantification of flow and perfusion is desirable, keeping the imaging target in a stationary status is difficult and, in some clinical scenarios, is not even possible. For example, such as imaging the distribution of blood flow velocity and flow rate for quantifying perfusion in coronary arteries and myocardium of a beating heart. Unfortunately, most conventional laser-based perfusion technologies either assume the target tissue/organ is stationary, which introduces significant inaccuracy or error in the clinical measurement of blood speed or velocity where the target is moving, such as a beating heart, or simply provide no information for quantification of perfusion in terms of blood flow rate distribution that is critically needed in the clinical situation where the target may or may not be moving.

Tissues/organs in animals or humans respond differently to light of different wavelengths. In general, light of shorter wavelengths can penetrate only the superficial layers of the tissues while light of longer wavelengths can penetrate both superficial layers and sub-surface layers in the spectral region from ultraviolet (UV) to near-infrared (NIR). UV and visible light of wavelengths less than, for example, 550 nm is optimal for detailed anatomic visualization in medicine when viewing the surface of tissues and organs. However, unlike NIR light, UV or visible light imaging is usually not inherently capable of revealing the physiological characteristics of tissues/organs in sub-surface layers, in part due to lack of penetration of the tissues/organs. Accordingly, improved methods of visualization and quantification are desired.

SUMMARY

Some embodiments of the present inventive concept provide a multispectral imaging system including a first light source, the first light source being one of coherent, non-coherent and partially coherent, the first light source having a first wavelength configured to produce a non-coherent illumination to image a sample; a second coherent light source, different from the first light source, having a second wavelength, different from the first wavelength, configured to image the sample simultaneously with the first light source; a camera configured to simultaneously receive information related to the first and second light sources from the sample, wherein light at the first wavelength is configured to image a surface of the sample into the camera and light at the second wavelength is configured to penetrate the sample and provide information related to the penetrated sample to the camera; and a processor configured to combine the received information related to the first and second light sources and generate a synthesized image of the anatomical structure and the physiology of blood flow and perfusion of the sample in terms of blood flow rate distribution.

In further embodiments of the inventive concept may also include additional coherent or non-coherent light sources of different wavelengths that specifically interact with hemoglobin (Hgb) in the blood, and where the absorbance of these wavelengths is dependent upon the concentration of oxygenated hemoglobin and deoxygenated hemoglobin in the blood. These may be additional light sources or include the first and/or second light sources. These absorbance data are captured in conjunction with the first and second light sources to produce a synthesized image of the peripheral oxygen saturation in the target tissues being imaged. In still further embodiments of the inventive concept, a determination of hemoglobin concentration [Hgb] may be made from the absorbance data related to the relative concentration and relative concentration change of deoxygenated hemoglobin [Hb] and oxyhemoglobin [HbO2].

In still further embodiments to the inventive concept a presentation of both the blood flow distribution and the peripheral oxygen saturation images together may be provided. Thus, data on perfusion, oxygen saturation, and hemoglobin concentration in the target tissues of interest may be presented simultaneously.

Some embodiments of the present inventive concept provide methods for obtaining a multispectral imaging system, the method including imaging a sample with a least one first light source having at least one first wavelength configured to produce a non-coherent illumination for a first period of time; imaging the sample with at least one second coherent light source, different from the at least one first light source, having at least one second wavelength, different from the at least one first wavelength, for a second period of time, wherein the first and second period of time do not overlap; receiving information related to the at least one first and second light sources from the sample; and combining the received information related to the at least one first and second light sources; and generating synthesized images of the sample illustrating at least peripheral oxygen saturation ($SpO_2$) associated with the sample.

BRIEF DESCRIPTION OF THE DRAWINGS

FIGS. 7A and 7B are images illustrating the perfusion measurement using only near infra-red light (7A) and dual wavelength illumination 7B) of a moving hand.

FIGS. 8A and 8B are images illustrating the perfusion measurement using only near infra-red light (8A) and dual wavelength illumination (8B) of a stationary hand with blood supply temporarily occluded by inflating an ipsilateral blood pressure cuff.

DETAILED DESCRIPTION

Figure 1A:
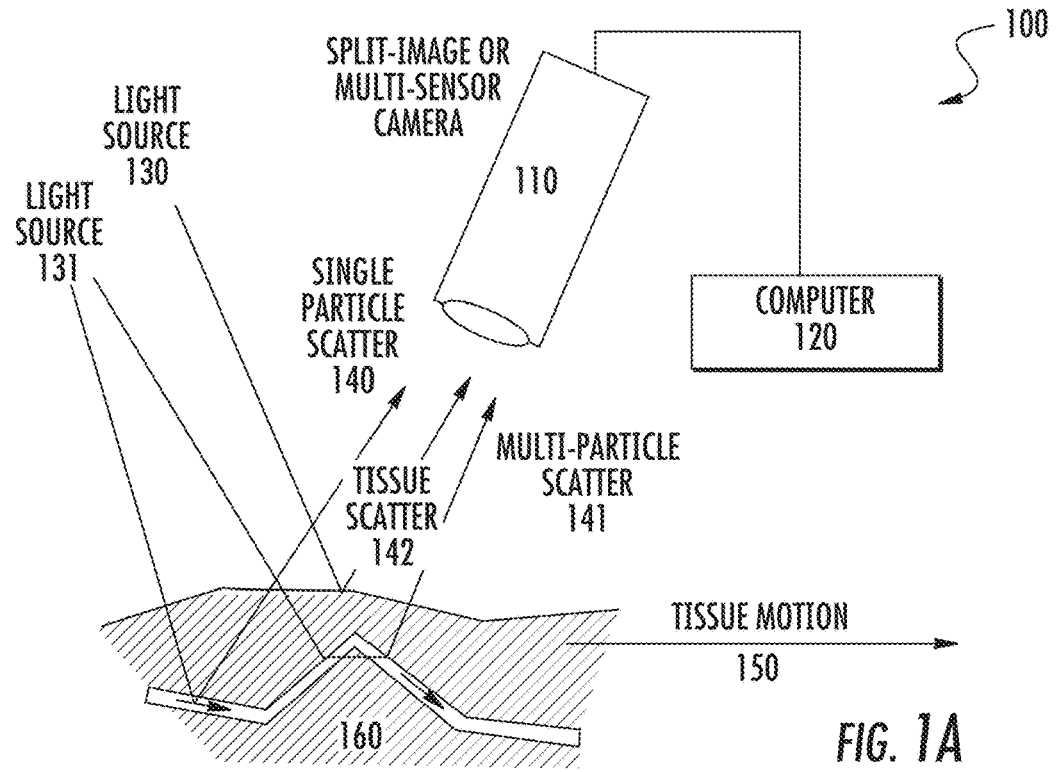
FIG. 1A is a block diagram illustrating a system implementing dual wavelength imaging in accordance with some embodiments of the present inventive concept.

Embodiments of the present inventive concept will now be described more fully hereinafter with reference to the accompanying Figures, in which preferred embodiments of the inventive concept are shown. This inventive concept may, however, be embodied in many different forms and should not be construed as limited to the embodiments set forth herein. Like numbers refer to like elements throughout. In the Figures, layers, regions, elements or components may be exaggerated for clarity. Broken lines illustrate optional features or operations unless specified otherwise.

The terminology used herein is for the purpose of describing particular embodiments only and is not intended to be limiting of the inventive concept. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y." The term "about" means the numerical value can vary by plus or minus ten percent.

Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled"

with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the inventive concept. The sequence of operations (or steps) is not limited to the order presented in the claims or Figures unless specifically indicated otherwise.

Spatially relative terms, such as "under", "below", "lower", "over", "upper" and the like, may be used herein for ease of description to describe one element or feature's relationship to another element(s) or feature(s) as illustrated in the Figures. It will be understood that the spatially relative terms are intended to encompass different orientations of the device in use or operation in addition to the orientation depicted in the Figures. For example, if a device in the Figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

As will be appreciated by one of skill in the art, embodiments of the present inventive concept may be embodied as a method, system, data processing system, or computer program product. Accordingly, the present inventive concept may take the form of an embodiment combining software and hardware aspects, all generally referred to herein as a "circuit" or "module." Furthermore, the present inventive concept may take the form of a computer program product on a non-transitory computer usable storage medium having computer usable program code embodied in the medium. Any suitable computer readable medium may be utilized including hard disks, CD ROMs, optical storage devices, or other electronic storage devices.

Computer program code for carrying out operations of the present inventive concept may be written in an object oriented programming language such as Matlab, Mathematica, Java, Smalltalk, C or C++. However, the computer program code for carrying out operations of the present inventive concept may also be written in conventional procedural programming languages, such as the "C" programming language or in a visually oriented programming environment, such as Visual Basic.

It will be understood that some embodiments of the present inventive concept implemented in Matlab may provide improved processing speeds in accordance with some embodiments of the present inventive concept.

Certain of the program code may execute entirely on one or more of a user's computer, partly on the user's computer, as a standalone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider).

The inventive concept is described in part below with reference to flowchart illustrations and/or block diagrams of methods, devices, systems, computer program products and data and/or system architecture structures according to embodiments of the inventive concept. It will be understood that each block of the illustrations, and/or combinations of blocks, can be implemented by computer program instructions. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the block or blocks.

These computer program instructions may also be stored in a computer readable memory or storage that can direct a computer or other programmable data processing apparatus to function in a particular manner, such that the instructions stored in the computer-readable memory or storage produce an article of manufacture including instruction means which implement the function/act specified in the block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the block or blocks.

The present inventive concept relates generally to blood flow and perfusion quantification and, more particularly, to quantification of blood flow and perfusion in tissue/organs in terms of distributions of blood velocity and blood flow rate using imaging techniques, such as Laser Speckle Imaging (LSI), Laser Doppler Imaging (LDI), Florescence imaging, reflectance imaging and the like with multispectral capability. Some embodiments of the inventive concept use two or more wavelengths in the range from 350 nm to 1100 nm to measure/quantify the blood velocity and blood flow rate distributions for quantification of perfusion, remove motion artifact and enhance visualization for presentation and real-time evaluation and assessment of the synthesized anatomical-physiological result. As used here, "Multispectral Laser Imaging (MSLI)" refers to imaging techniques using two or more wavelengths in accordance with some embodiments of the present inventive concept. For example, MSLI techniques are discussed in commonly assigned U.S. patent Ser. No. 10/058,256 entitled Multi-Spectral Laser Imaging (MSLI) Methods and Systems for Blood Flow and Perfusion Imaging and Quantification, to Chen et al., the disclosure of which is hereby incorporated herein by reference as if set forth in its entirety.

In particular, some embodiments of the present inventive concept provide a system that uses two wavelengths (or wavelength ranges) of differential transmittance through a sample to apply laser speckle or laser Doppler imaging. A first of the two wavelengths may be relatively small within the UV or visible range, such as blue light 450-495 nm. Light at this wavelength has very shallow penetration and images the anatomical structure of tissue/organ surface and serves as a position marker of the sample but not the subsurface movement of blood flow and perfusion. A second wavelength may be relatively large in the visible (400-700 nm) or near Infra-Red (NIR) range (700-2500 nm). Light at this wavelength has much larger penetration depth and reveals the underlying blood flow physiology and correlates both to the motion of the sample and also the movement of blood flow and perfusion. Using the imaging measurement of the visible light as a baseline, the true motion of blood flow and perfusion can be derived from the NIR imaging measurement without being affected by the motion artifact of the target. Furthermore, the anatomical structure information captured by visible light and the physiological characteristics measured by NIR light is combined as will be discussed herein.

As discussed in the background of the present application, using only visible or NIR spectrums may result in various issues with the final images produced. Accordingly, some embodiments of the present inventive concept combine different wavelengths of visible and NIR spectrum (350 nm-1100 nm) into an imaging system, such as LSI, LDI, Fluorescence, Reflectance or LSI plus Fluorescence and the like. The combination, as discussed herein, may reveal much more information of the tissue/organ than using one single wavelength. In particular, MSLI in accordance with some embodiments discussed herein can, for example, (1) account for and remove the motion artifact present in imaging clinical biologic structures, which creates blood flow and perfusion quantification inaccuracies; (2) improve visualization over current technologies by exact synthesis of both anatomic structure and the physiology of blood flow and perfusion simultaneously in real time; (3) through a combination of (1) and (2), improve the accuracy of quantification of blood flow and perfusion in clinical applications as will be discussed herein with respect to FIGS. 1A through 24.

As used herein. "real time" refers to provision of data within a very short amount of time, for example, milliseconds, so as to appear as if the data was provided immediately upon request or activation of light sources.

In some embodiments, in addition to using multiple wavelengths over the visible and NIR spectrum (350-1100 nm), embodiments of the present inventive concept can, for example, combine two or more laser imaging techniques such as near infra-red fluorescence (NIRF) and Laser Speckle Imaging (LSI), or NIRF and Laser Doppler Imaging (LDI), into one system as will also be discussed below with respect to the Figures.

Furthermore, some embodiments of the present inventive concept provide the ability to apply methods of visualization and quantification across multiple clinical and experimental settings. These settings include direct illumination and imaging of tissues, but where access to the imaged Field of View (FOV) is accomplished through different approaches. These approaches may include, for example, direct contact or non-contact with tissues, exposure of the tissues during open surgical procedures, or via endoscopy to access tissues within closed anatomic structures or tissues in the alimentary tract or tracheobronchial tree without departing from the scope of the present inventive concept.

As used herein, "blood flow rate distribution" refers to a relation between velocity distribution of u (the velocity vector, in m/sec) in the region of interest or field of view (FOV) and the blood flow distribution. Calculation of blood flow rate distribution (volume flow in cc/min) involves using tools such as computational fluid dynamics models to obtain blood flow rate (a surface integral of the u vector over the cross section of a vessel) from a measured distribution of velocity u. Furthermore, embodiments of the present inventive concept are configured for macro FOVs of, for example, about 100 mm×about 100 mm.

Figure 1B:
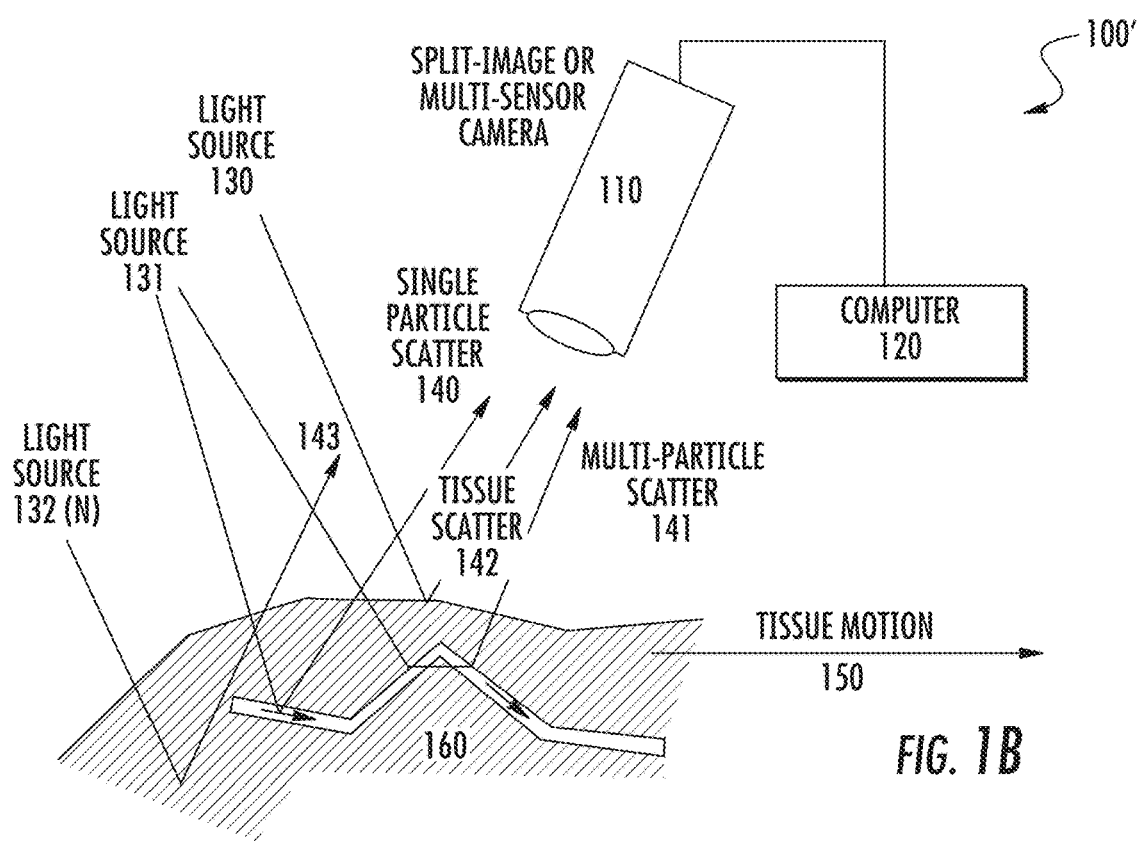
FIG. 1B is a block diagram illustrating a system including a plurality of light sources in accordance with some embodiments of the present inventive concept.
Figure 1C:
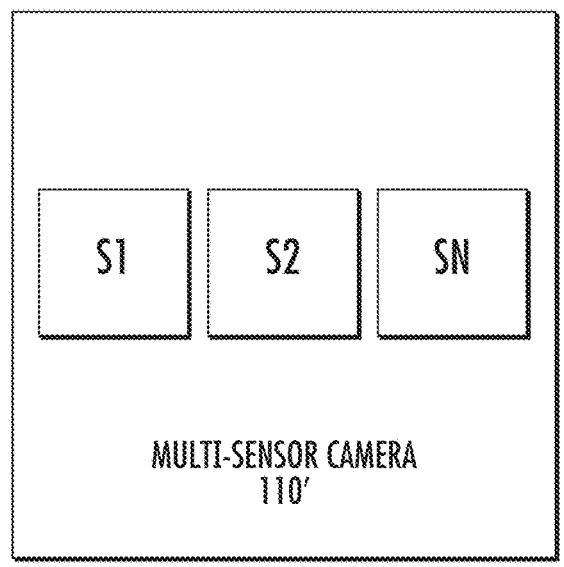
FIG. 1C is a block diagram illustrating a multi-sensor camera in accordance with some embodiments of the present inventive concept.

Referring first to FIG. 1A, a block diagram illustrating a simple system implementing dual wavelength imaging in accordance with some embodiments of the present inventive concept will be discussed. As illustrated in FIG. 1A, the system 100 includes at least two light sources, first 130 and second 131 light sources, respectively, a sample 160, a camera 110 and a communications device (computer 120). In some embodiments of the present inventive concept, the first light source 130 delivers visible light and the second light source 131 delivers NIR light. As discussed above, the coherent short wavelength (visible source 130) does not penetrate deep into the sample 160 (tissue/organ) but provides detail of the surface of the sample 160 in the tissue scatter (142). In contrast, the coherent NIR source 131 penetrates deep into the sample 160 and may provide single (140) or multi particle scatter (141). The reflections 140, 141, 142 off the sample 160 are captured by a camera 110, which may be, for example, a split-image or multi-sensor camera in some embodiments. In particular, in some embodiments the camera may be a multi-sensor camera, rather than a single camera with one sensor chip. The multi-sensor camera has multiple sensors and each sensor may be configured to image one wavelength or wavelength range. As illustrated in FIG. 1C, in embodiments having a multi-sensor camera 110', the camera may have a plurality of spaced apart sensors S1 through SN. Each sensor may be configured to image one wavelength or wavelength range. The number "N" in S1-SN can be any reasonable number in accordance with embodiments discussed here. For example, "N" may be between 2 and 50 without departing from the scope of the present inventive concept.

The information can be processed by the communications device 120, which combines the visible and NIR wavelength images to provide improved blood flow and perfusion data in accordance with some embodiments of the present inventive concept. As will be understood, the data provided by embodiments discussed herein account for movement 150 of the sample (tissue/organ) 160 and provide an improved image thereof relative to conventional images.

Although some embodiments are discussed herein as having two wavelengths, embodiments of the present inventive concept are not limited to this configuration. For example, as illustrated in FIG. 1B, in some embodiments, at least a third light source 132 is provided having a third wavelength and this wavelength may penetrate the sample at a different depth than the first and second wavelengths and provide a different scatter pattern 143. In some embodiments, the at least third wavelength may be configured to assess specific physiologic parameters, for example, Hgb concentration. It will be understood that there may more than three light sources in some embodiments.

Thus, in some embodiments a plurality of first light sources may be used for the MSPV portion of the inventive concept and a second plurality of light sources may be used for the SpO$_2$ portion of the inventive concept. The wavelengths used to obtain the MSPV data may interfere with the wavelengths used to obtain the SpO$_2$ data. Therefore, in some embodiments the MSPV light sources and the SpO$_2$ light sources may be turned on and/or off at intervals to reduce the likelihood of interference as will be discussed further below.

Figure 2:
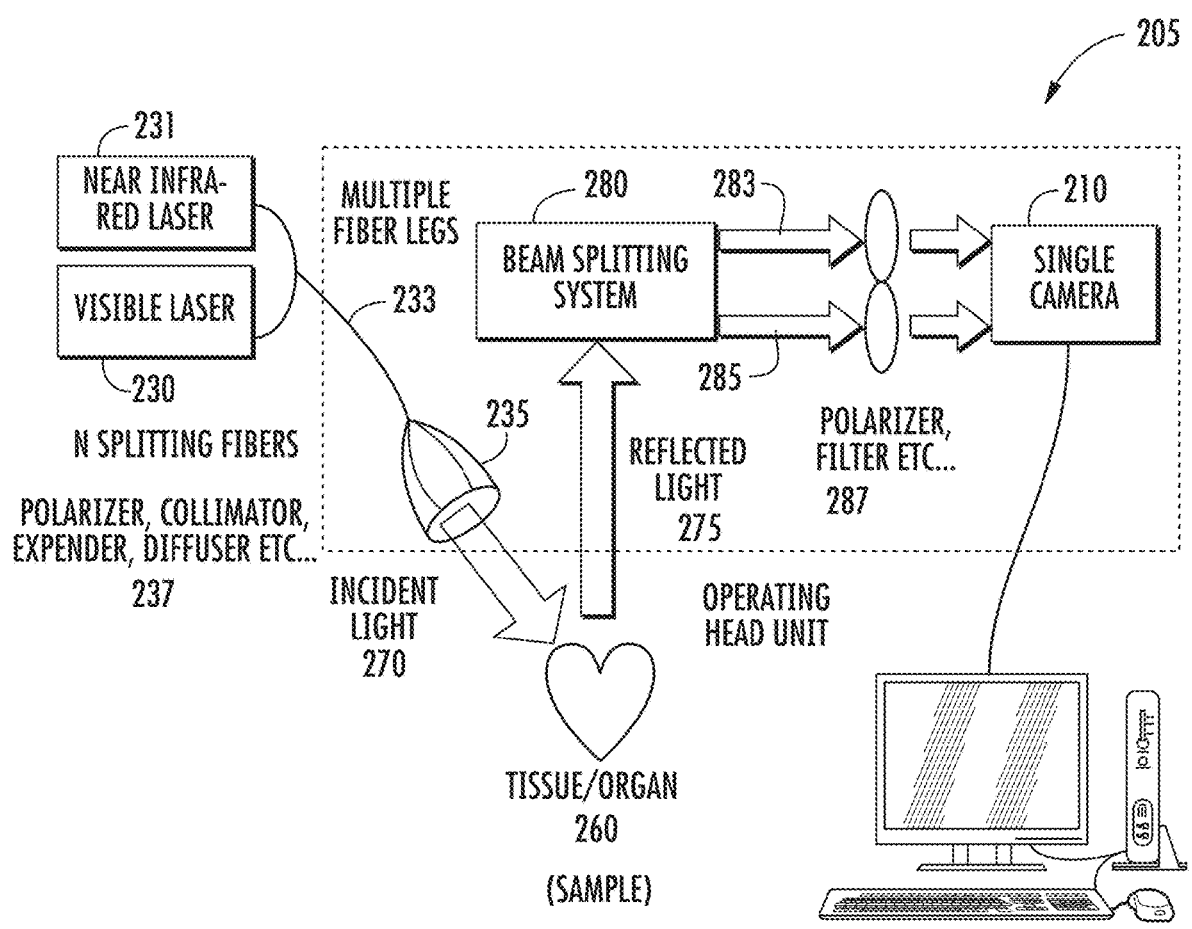
FIG. 2 is a more detailed block diagram illustrating various components of a multi-wavelength imaging system in accordance with some embodiments of the present inventive concept.

Referring now to FIG. 2, an example of embodiments wherein a light source provides physiologic parameters will be discussed. FIG. 2 is a block diagram illustrating various components of a multi-wavelength imaging system in accordance with some embodiments of the present inventive concept. As illustrated in FIG. 2, the system 205 includes at least two laser light sources, visible 230 and NIR 231, a connecting fiber 233, components of an imaging system 237, a sample 260, a beam splitter 280, a camera 210 and a communications device (computer system 220). In operation, when the NIR laser delivers NIR light to a living sample 260, such as a tissue/organ, a portion of the NIR light will go through single or multiple scattering of both stationary and moving particles inside the sample and reflect back. When the visible laser 230 delivers non-penetrating visible light, such as light having 430 nm, to a living sample 260, such as a tissue/organ, most of the light will be reflected back by the surface within less than 100 µm depth. For the NIR laser 231, approximately ninety five percent of the light will be returned from a top 700 µm of the sample 260, which is enough penetration to pass through coronary artery walls at, for example, a 300 µm depth, and generate information from moving particles, such as red blood cells, as well as from stationary tissue.

The reflected visible light contains the surface movement information of the sample 260 and, thus, reflects the motion artifact. The reflected NIR light contains the surface and subsurface movement information of the sample 260 and, thus, reflects both motion artifact and movement of the blood flow. As illustrated in FIG. 2, the light produced by the lasers 230 and 231 may be provided to a fiber 233, which may have multiple fiber legs and may include a plurality of splitting fibers 235 as illustrated. However, embodiments of the present inventive concept are not limited to the configuration illustrated in FIG. 2. For example, more or less fibers may be used without departing from a scope of the present inventive concept. Furthermore, the light on the fibers may pass through various elements of an imaging system 237 before reaching the sample 260. For example, the light may traverse polarizers, collimators, expanders, diffusers and the like before reaching the sample 260 without departing from the scope of the present inventive concept. It will be understood that many different variations of imaging systems 237 may be used in combination with embodiments discussed herein.

The incident light 270 illuminates the sample 260 and the reflected light 275 is provided to a beamsplitter 280. In some embodiments of the present inventive concept, the beamsplitter 280 may be a dichroic beam splitting system that separates the NIR 283 and visible light 285. The separated light 283 and 285 may pass through polarizers, filters and the like 287 before being delivered to the camera 210. As discussed above, the camera 210 can be, for example, a split-image (single sensor) or multi-sensor camera without departing from the scope of the present inventive concept. As stated, the multi-sensor camera has multiple sensors each configured to image a wavelength or wavelength range as illustrated in FIG. 1C.

The NIR 283 and visible 285 images are directed to the camera 210 and a split image is created on one camera sensor or on separate camera sensors S1-SN (FIG. 11C) that have been synchronized and aligned. As discussed above, different wavelengths have different penetration levels in the tissue/organ. Using multi-spectrum image design as discussed herein, the anatomical structure and blood flow physiology at different depths in the tissue/organ can be revealed as will be discussed below with respect to various Figures.

Figure 3:
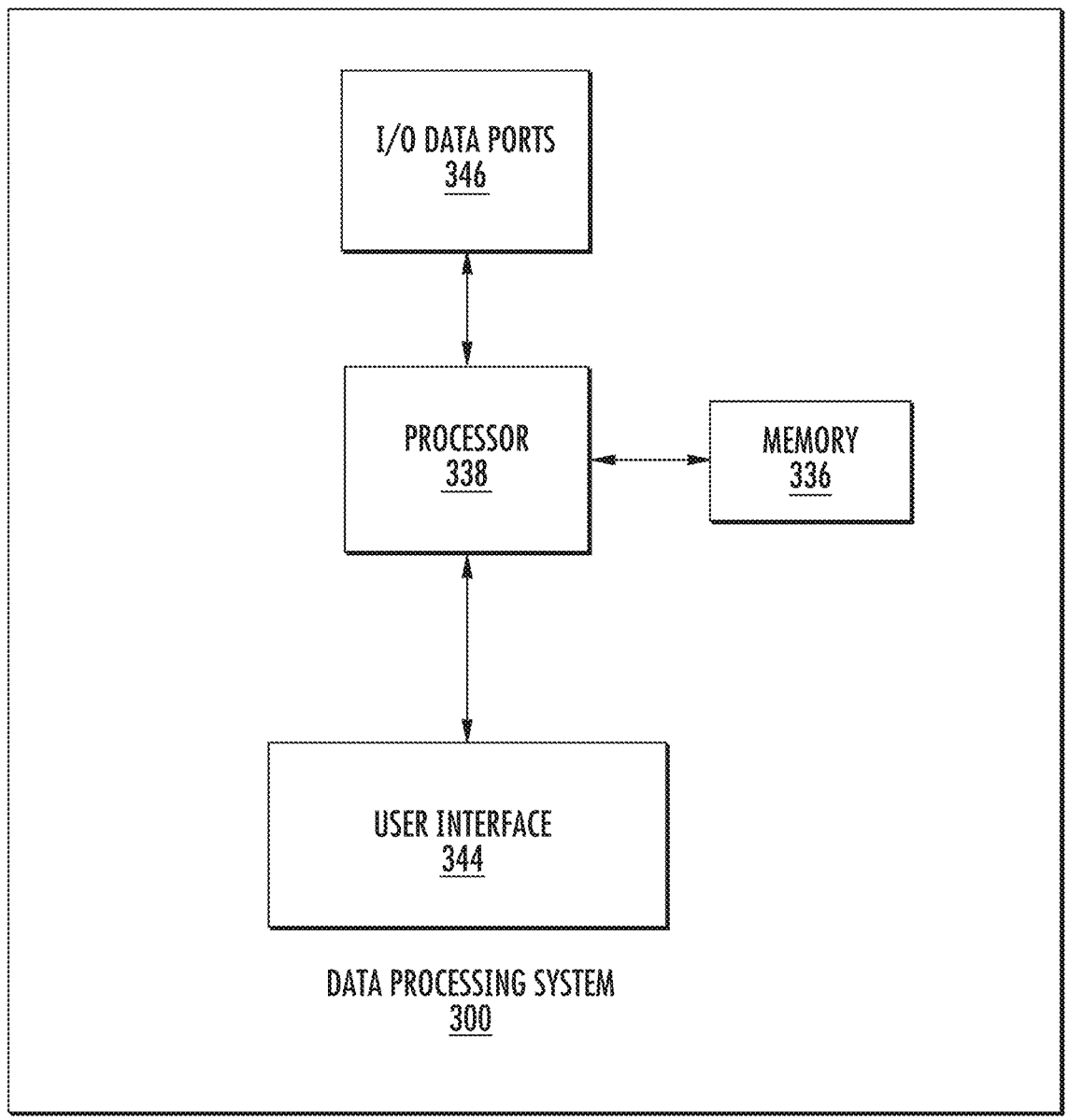
FIG. 3 is a block diagram of a data processing system according to some embodiments of the present inventive concept(s).

As illustrated in FIGS. 1A, 1B and 2, systems in accordance with embodiments of the present inventive concept include communications devices 120, 220, which are used for the various processing necessary to implement embodiments of the present inventive concept. Referring now to FIG. 3, a data processing system 300 that may be used in the systems of FIGS. 1 and 2, for example, in the communications devices 120, 220, in accordance with some embodiments of the inventive concept will be discussed. It will be understood that the data processing system 300 may be included in any of the components of the system without departing from the scope of the present inventive concept. For example, the data processing system 300 may be included in the camera 110, 210 or split between various elements of the system without departing from the scope of the present inventive concept.

Referring now to FIG. 3, an exemplary embodiment of a data processing system 300 suitable for use in the systems of FIGS. 1A, 1B and 2 includes a user interface 344 such as a keyboard, keypad, touchpad or the like, I/O data ports 346 and a memory 336 that communicates with a processor 338. The I/O data ports 346 can be used to transfer information between the data processing system 300 and another computer system or a network. These components may be conventional components, such as those used in many conventional data processing systems, which may be configured to operate as described herein.

Figure 4:
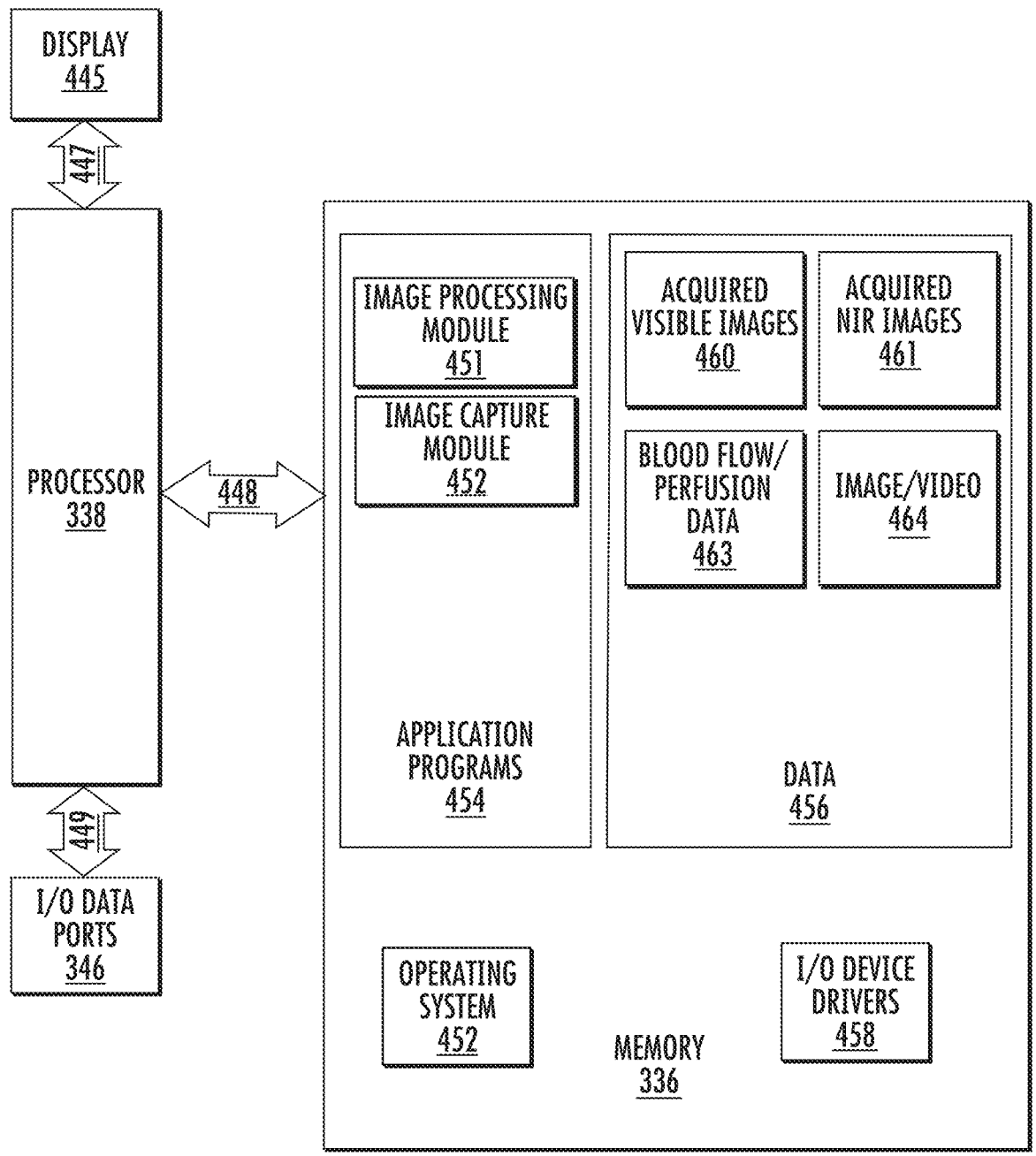
FIG. 4 is a more detailed block diagram of the data processing system illustrated in FIG. 3 in accordance with some embodiments of the present inventive concept(s).

Referring now to FIG. 4, a more detailed block diagram of the data processing system 300 in accordance with some embodiments of the present inventive concept will be discussed. The processor 338 communicates with a display 445 via and address/data bus 447, the memory 336 via an address/data bus 448 and the I/O data ports 346 via an address/date bus 449. The processor 338 can be any commercially available or custom microprocessor or ASICs. The memory 336 is representative of the overall hierarchy of memory devices containing the software and data used to implement the functionality of the data processing system 300. The memory 336 can include, but is not limited to, the following types of devices: cache, ROM, PROM, EPROM, EEPROM, flash memory, SRAM, and DRAM.

As illustrated in FIG. 4, the memory 336 may include several categories of software and data used in the data processing system 300: an operating system 452; application programs 454; input/output (I/O) device drivers 458; and data 456. As will be appreciated by those of skill in the art, the operating system 452 may be any operating system suitable for use with a data processing system, such as OS/2, AIX or zOS from International Business Machines Corporation, Armonk, N.Y., Windows95, Windows98, Windows2000, WindowsXP, or Vista from Microsoft Corporation, Redmond, Wash., Unix, Linux, LabView, or a real-time operating system such as QNX or VxWorks, or the like. The I/O device drivers 458 typically include software routines accessed through the operating system 452 by the application programs 454 to communicate with devices such as the I/O data port(s) 346 and certain memory 336 components. The application programs 454 are illustrative of the programs that implement the various features of the data processing system 300 included in a system in accordance with some embodiments of the present inventive concept and preferably include at least one application that supports operations according to some embodiments of the present inventive concept. Finally, the data 456 represents the static and dynamic data used by the application programs 454, the operating system 452, the I/O device drivers 458, and other software programs that may reside in the memory 336.

As illustrated in FIG. 4, the data 456 according to some embodiments of the present inventive concept may include acquired visible images 460, acquired NIR images/data 461, calculated blood flow/perfusion data 463 and images/video 464. Although the data 456 illustrated in FIG. 4 includes four different files 460, 461, 463 and 464, embodiments of the present inventive concept are not limited to this configuration. Two or more files may be combined to make a single file; a single file may be split into two or more files and the like without departing from the scope of the present inventive concept.

As further illustrated in FIG. 4, the application programs 454 may include an image processing module 451 and an image capture module 453 in accordance with some embodiments of the inventive concept. While the present inventive concept is illustrated, for example, with reference to the image processing module 451 and the image capture module 453 being application programs in FIG. 4, as will be appreciated by those of skill in the art, other configurations may also be utilized while still benefiting from the teachings of the present inventive concept. For example, the image processing module 451 and the image capture module 453 may also be incorporated into the operating system 452 or other such logical division of the data processing system 300. Thus, the present inventive concept should not be construed as limited to the configuration of FIG. 4 but is intended to encompass any configuration capable of carrying out the operations described herein.

Furthermore, while the image processing module 451 and the image capture module 453 are illustrated in a single data processing system, as will be appreciated by those of skill in the art, such functionality may be distributed across one or more data processing systems. Thus, the present inventive concept should not be construed as limited to the configurations illustrated in FIGS. 3 and 4 but may be provided by other arrangements and/or divisions of function between data processing systems.

In certain embodiments, such as an LSI application, the velocity of a target fluid can be calculated using the following equation:

$$v(i, j) = v_0 + \frac{a}{c(i, j)^2} \qquad \text{Eqn. (1)}$$

where v(i,j) is the velocity of target fluid, v0 is an added term to account for background noise and may be zero after the baseline has been removed; a is a constant related to imaging parameters, laser parameters, time/spatial smoothing parameters for obtaining c and reflects the optical characteristics of the target fluid; c is the laser speckle contrast; and i and j are the row and column pixel index.

For an LDI application, the velocity of a target fluid can be calculated using the following equation:

$$v(i, j) = \frac{\lambda}{2\sin\theta}\Delta f \qquad \text{Eqn. (2)}$$

where v(i,j) is velocity of target fluid; where $\lambda$ is the wavelength; $\Delta f$ is the change in Doppler frequency (Doppler frequency shift); and $\theta$ is half of the angle between the two beams. Typically, there is no direct formula to apply for NIRF, and the like.

However, even when the imaged object is stationary, there is movement present that must be accounted for to accurately determine blood flow in vessels and perfusion in tissue. As recently as 2013, experts in the field of LSI discussed motion artifact as one of the two key questions still to be answered in this field. Therefore, systems and methods that have the capability to identify this motion contribution and account for its magnitude are needed and included in technologies claiming to be able to assess, image, and/or quantify blood flow in vessels and perfusion in tissues experimentally and in vivo.

Figure 5A:
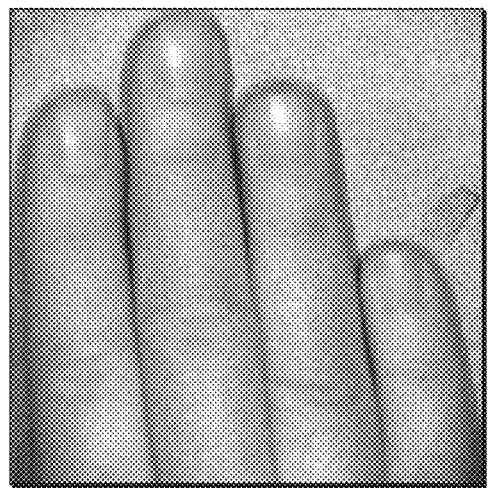
FIGS. 5A and 5B are a visible light image (5A) and a near infra-red light image (5B) of a hand.
Figure 5B:
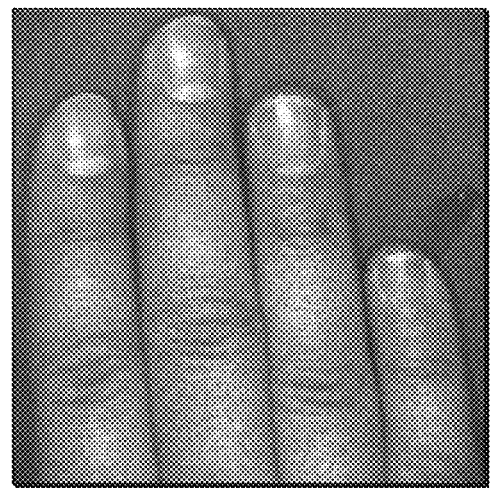

Referring now to FIGS. 5A and 5B, FIG. 5A is a visible light image of a hand and FIG. 5B is a near infra-red light image of a hand. These images may be used to calculate the motion artifact and the movement of the blood flow and perfusion in accordance with some embodiments of the present inventive concept.

In particular, to remove the motion artifact of the tissue/organ that is caused by movement of tissue/organ, such as aspiration, spasm, heart beat and the like and/or the camera, Galilean velocity addition can be calculated using the following equation:

$$v12(r) = v13(r) + v32(r) = v13(r) - v23(r) \qquad \text{Eqn. (3)}$$

where: v13(r) is the velocity distribution of object of interest (blood flow and perfusion) relative to detector (camera); v23(r) is the velocity distribution of the host object (the tissue/organ in which the blood vessel is embedded) relative to detector (camera); v32(r) is the velocity distribution of the detector (camera) relative to the host object (the tissue/organ in which the blood is embedded); and v12(r) is the velocity distribution of an object of interest (blood flow and perfusion) relative to the host object (the tissue/organ in which the blood vessel is embedded). Thus, embodiments of the present inventive concept may address a need to determine v12(r) under the condition that the image signals by the all the current LSI or LDI method provides only v13(r). According to some embodiments of the present inventive concept, the multi spectrum imaging approach, both v13(r) and v23(r) can be made available.

Using LSI as an example, using the Eqn. (1) above, the speckle contrast of coherent NIR laser light $C_{NIR}(i,j)$ is associated with v13(r), which is the velocity distribution of an object of interest (blood flow and perfusion) relative to detector (camera). v13(r) is affected by the movement of blood flow and the movement of tissue/organ caused by factors such as aspiration, spasm, heart beat etc. and the movement of the camera. The visible laser light, especially within the 450-495 nm wavelength range (blue laser light), has much less penetration in soft tissue/organ compared with the NIR laser light.

Using Eqn. (1) set out above, the speckle contrast of coherent visible laser light $C_{VIS}(i,j)$ is mainly associated with v23(r), which is the velocity distribution of the host object (the tissue/organ that the blood vessel is embed) relative to detector (camera). v23(r) is affected by the movement of tissue/organ caused by factors such as aspiration, spasm, heart beat etc. and the movement of the camera. Using Eqn. (3), v12(r) can be derived using v13(r) and v23(r) thus the velocity distribution of object of interest (blood flow and perfusion) relative to the host object (the tissue/organ that the blood vessel is embed) can be quantified without the effect of the movement of tissue/organ and the movement of the camera.

The speckle contrast of coherent visible laser light $C_{VIS}$ (i,j) as a baseline can be used to normalize the speckle contrast of coherent NIR laser light $C_{NIR}$(i,j) based on this mathematic model to reduce the velocity component of the motion artifact. Computer algorithms may be designed to normalize (subtract or divide) $C_{NIR}$(i,j) using $C_{VIS}$(i,j) to yield one or multiple stabilized blood flow and perfusion maps in real time. The algorithms may be processed by, for example, a data processor as discussed above with respect to FIGS. 3-4.

Figure 6A:
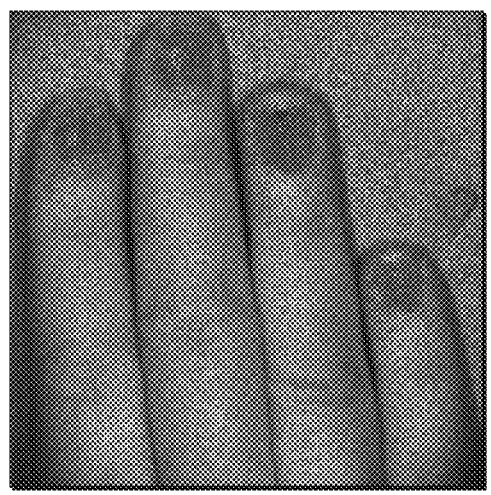
FIGS. 6A and 6B are images illustrating the perfusion measurement using only near infra-red light (6A) and dual wavelength illumination (6B) of a stationary hand.
Figure 6B:
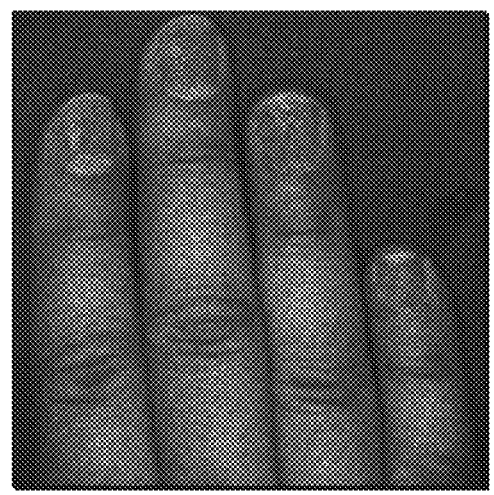

Referring now to FIGS. 6A and 6B, images generated using the measurement of the blood flow and perfusion using only NIR and dual wavelength illumination of a stationary hand will be discussed. As illustrated, the measurement of the blood flow and perfusion using only NIR and dual wavelength illumination of a stationary hand are very similar. This is because when the sample/target is stationary, the motion artifact as baseline measured by visible light is close to zero. Thus, the result without removing the baseline (FIG. 6A: using only NIR light) and the result with the baseline removed (FIG. 6B: using dual wavelength illumination) are almost identical.

Referring now to FIGS. 7A and 7B, images illustrating the measurement of the blood flow and perfusion using only NIR and dual wavelength illumination of a moving hand will be discussed. As illustrated therein, the measurement of the blood flow and perfusion using only NIR and dual wavelength illumination of a shaking hand are very different. The measurement with only NIR light (FIG. 7A) shows much higher perfusion level which is caused by the motion artifact. The measurement with dual wavelength illumination (FIG. 7B) is almost identical to the measurement of the stationary hand. This is because when the sample/target is moving the motion artifact as baseline measured by visible light is not zero. Thus, the result without removing the baseline (FIG. 7A: using only NIR light) shows more "blood flow and perfusion" than the result with the baseline removed (FIG. 7B: using dual wavelength illumination).

Referring now to FIGS. 8A and 8B, images illustrating both the perfusion measurement with only NIR and the dual wavelength illumination will be discussed. In particular, FIGS. 8A and 8B are images illustrating the perfusion measurement using only near infra-red light (8A) and dual wavelength illumination (8B) of a stationary hand with blood supply temporarily occluded by squeezing the wrist of the imaged hand using the other hand. As illustrated, a decrease induced by the temporary occlusion of the blood supply to the hand is clear.

Different from LSI, LDI uses interference of two coherent light beams: the one from the laser as the light source and the one reflected from the moving object whose frequency is slightly shifted from that of the incident light. LDI determines the speed of one "pixel" or points or a small region of the object where the incident beam is focused on. An image is obtained by scanning the focused beam. Similar to the LSI of Eqn. (1) using Eqn. (2), measurement of v13(r) and v23(r) in LDI can be achieved using a penetrating NIR beam and a non-penetrating visible beam. Again, using Eqn. (3) v12(r) of the fiducial points relative to the host object (the tissue/organ that the blood vessel is embed) can be identified.

Figure 9A:
FIGS. 9A and 9B are images illustrating perfusion measurement using only near infra-red light (9A) and dual wavelength illumination (9B) of a large bowel of a pig.
Figure 9B:
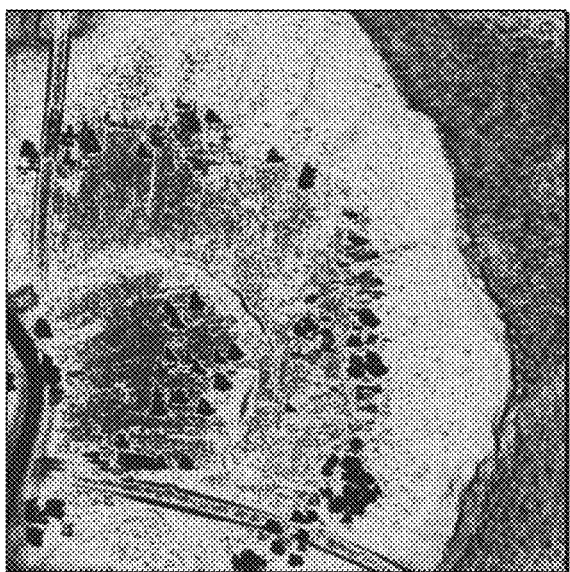

Furthermore, practically, the laser speckle contrast is a mixture of static background and dynamic part. The dynamic part of the speckle contrast is associated with the motion and the static background is caused by the difference of the optical characteristics of the inhomogeneous scattering media. Since among the current LSI technologies, baseline speckle contrast at a no flow situation is not available, other than in a controlled phantom/tubing experiment, the static background of the speckle contrast is a major obstacle to accurately quantifying blood flow in tissue/organ. Multi-spectrum illumination schemes provide a baseline speckle contrast at no flow situation $C_{VIS}$(i,j) using visible coherent laser light. The speckle contrast of coherent visible laser light $C_{VIS}$(i,j) can be used to normalize the speckle contrast of coherent NIR laser light $C_{NIR}$(i,j) based a mathematic model in accordance with embodiments of the present inventive concept to reduce the static background in the speckle contrast as illustrated in FIGS. 9A and 9B. FIGS. 9A and 9B illustrate perfusion measurement using only near infra-red light (9A) and dual wavelength illumination (9B) of a large bowel of a pig. Measurement inaccuracy caused by the static contrast can be seen on the surgical drape 950 in FIG. 9A. In FIG. 9B, the "fake" blood flow and perfusion is not visible on the surgical drape 950 due to reduction of the static contrast.

Embodiments of the present inventive concept propose the visualization of both anatomical structure and blood flow physiology of the tissue and organ by one of two approaches. However, it will be understood that embodiments of the present inventive concept are not limited to the approaches discussed herein.

Figure 10A:
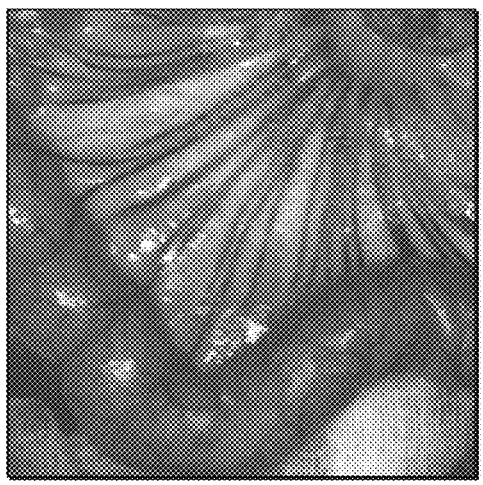
FIGS. 10A-10D are images illustrating a visible light image of a piece of small bowel of a pig as to define anatomical structure (10A); a near infra-red light image of the same piece of small bowel as to define the transparency map (10B); blood flow speed distribution map of the same piece of small bowel calculated by 11 frames of the NIR raw images using LSI (10C); and a combined visual effect using A, B, C using an algorithm in accordance with some embodiments of the present inventive concept to reveal both anatomical structure and blood flow physiology (10D).

Referring now to FIG. 10A-10D, a first approach using a dual layer design will be discussed. Referring first to FIG. 10A (Panel A), an anatomical layer represented by a raw (original) image frame of visible light is illustrated. (Anatomical layer) Img$_{VIS}$(i,j) is an 8 bit gray scale visible image of the sample/target tissue/organ and i and j are the pixel indexes along the horizontal and vertical direction. In some embodiments, the brightness, contrast and gamma value of this image might be adjusted to achieve better visualization effect.

Figure 10B:
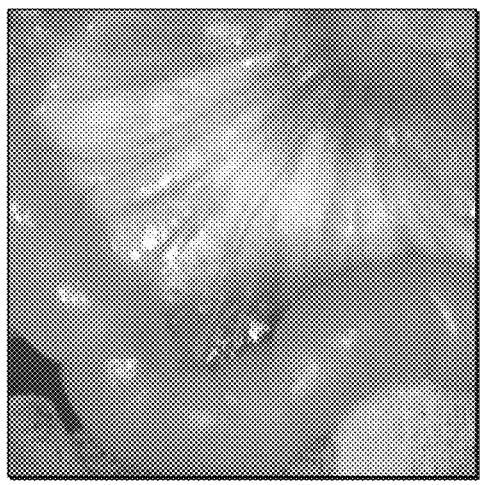

Referring now to FIG. 10B, a processed image is produced based on one or more raw image frames of near infra-red light to reflect two-dimensional (2D) speed distribution of blood flow and perfusion of the imaged tissue/organ using Laser Speckle or Laser Doppler Imaging technology. (Physiological layer) Img$_{NIR}$(i,j) is an 8 bit indexed image with its numerical values mapped to a predefined color map. Usually, the color ranges from blue to red (0 to 255) with blue representing no/minimum flow speed and red representing the highest flow speed that the system can detect.

Figure 10C:
Figure 10D:

Referring now to FIG. 10C, a transparency map is produced using methods that overlap the anatomical layer or parts of the anatomical layer over a physiological one, which will cause the bottom layer to be invisible (covered) or partially invisible (covered). Methods that overlap the physiological layer or parts of the physiological layer over anatomical one will cause the bottom layer to be invisible (covered) or partially invisible (covered). A transparency map/matrix is applied in accordance with embodiments of the present inventive concept to ensure the visibility of both layers using the following equation:

$$T(i, j) = \left( \frac{Img(i, j) - \text{Min}(Img(i, j))}{\text{Max}(Img(i, j)) - \text{Min}(Img(i, j))} \right)^x \qquad \text{Eqn.(4)}$$

where T(i,j) is the transparency map with Img being a raw (original) image frame of visible or near infra-red light and x being an adjustable parameter >0 and <=2. Basically, each pixel value in T(i,j) is between 0 and 1 with 0 representing no transparency and 1 representing 100% transparency. Parameter x controls the contrast of the transparency map and if x>1, transparency has a larger dynamic range and if x<1, the transparency has a smaller dynamic range. FIG. 10D represents the combined visual effect using A, B and C in accordance with embodiments of the present inventive concept to reveal both anatomical structure and physiology.

Figure 11A:
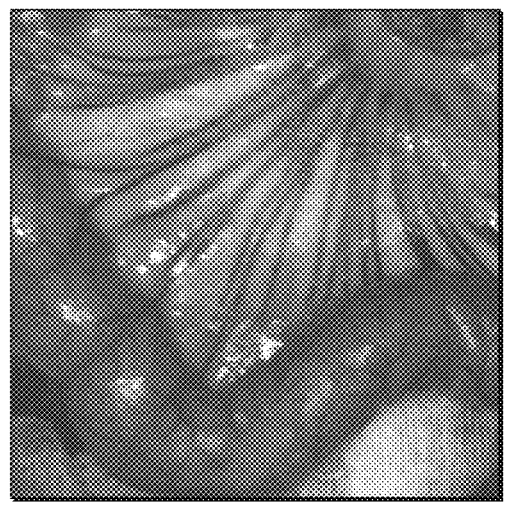
FIGS. 11A-11C are images illustrating a visible light image of a piece of small bowel of a pig as to define anatomical structure by the brightness of the 8 bit grayscale image (11A); blood flow speed distribution map of the same piece of small bowel calculated by 11 frames of the NIR raw images using LSI (11B); and a combined visual effect using A and B using an algorithm in accordance with some embodiments of the present inventive concept to reveal both anatomical structure and blood flow physiology (11C).
Figure 11B:
Figure 11C:
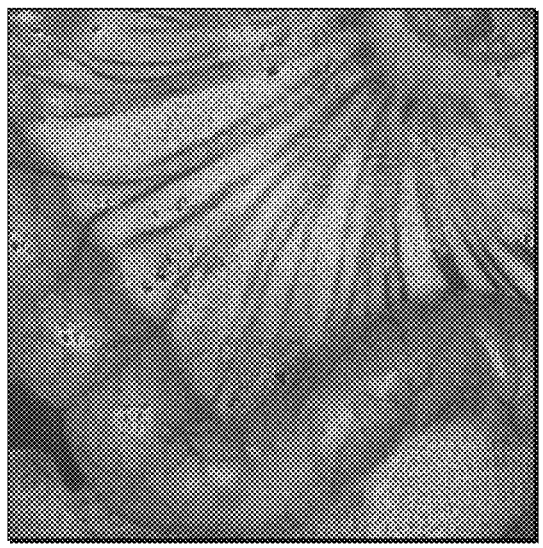

Referring now to FIGS. 11A through 11C, a second approach using color and brightness design will be discussed. As illustrated in FIG. 11A, an anatomical layer is represented by image brightness: a raw (original) image frame of visible light. $Img_{VIS}(i,j)$ is an 8 bit gray scale visible image of the sample/target tissue/organ and i and j are the pixel indexes along horizontal and vertical direction. The brightness, contrast and gamma value of this image may be adjusted to achieve better visualization effect.

Referring now to FIG. 11B, a physiological layer is represented by image color: a processed image based on one or more raw image frames of near infra-red light to reflect 2D speed distribution of blood flow velocity and perfusion of the imaged tissue/organ using Laser Speckle or Laser Doppler Imaging technology. In a first step, an 8 bit indexed color image is generated with its numerical values mapped to a predefined color map. Usually, the color ranges from blue to red (0 to 255) with blue representing no/minimum flow speed and red representing the highest flow speed that the system can detect. In a second step, the 8 bit indexed color image is converted to a normalized RGB map $RGB_{NIR}(i,j)$ with the color of each pixel being represented by (R, G, B) three values and each value range from 0-1. It will be understood that since the Figs. are in black and white, the corresponding grey scale has been employed herein.

Referring now to FIG. 11C, anatomical and physiological layers are fused together by creating an 8 bit RGB color image as $Img(i,j)=Img_{VIS}(i,j) \times RGB_{NIR}(i,j)$. Note, each color channel (matrix $R_{NIR}(i,j)$, $G_{NIR}(i,j)$ and $B_{NIR}(i,j)$) is multiplied by the same visible image $Img_{VIS}(i,j)$.

According to some embodiments of the present inventive concept, multi wavelength imaging design may be used to simultaneously combine different imaging technologies together. For example, as discussed herein, NIR fluorescence technology based on indocyanine green uses 808 nm illumination and the fluorescence emission light is 830 nm and 808 nm reflection light is considered as noise and filtered out. In accordance with some embodiments of the present inventive concept, the 808 nm reflection light can be used to achieve LSI or LDI while maintaining the 830 nm fluorescence function.

Referring now to FIGS. 12A-12D, images illustrating Panel A, an NIR 785 nm image of a small bowel (12A); Panel B a Green 532 nm image of the same small bowel (12B); Panel C, a reconstructed color image of the same small bowel (12C); and Panel D, an image of the same small bowel taken by a regular camera (12D) will be discussed. In particular, using the multi spectral imaging system in accordance with some embodiments of the present inventive concept, an original color image can be constructed by using each spectrum as one RGB color channel. For example, using an NIR image as a red color channel and a 532 nm image as a green color channel, the color image of a small intestine can be generated without using a color camera as illustrated in FIGS. 12A-12D. It will be understood that since the Figs. are black and white, the corresponding grey scale has been employed herein.

Figure 12A:
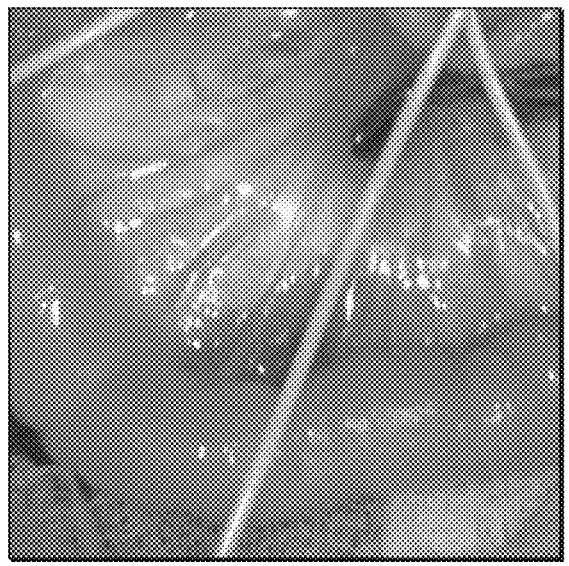
FIGS. 12A-12D are images illustrating Panel A, an NIR 785 nm image of a small bowel (12A); Panel B a Green 532 nm image of the same small bowel (12B); Panel C, a reconstructed image of the same small bowel (12C); and Panel D, an image of the same small bowel taken by a regular camera (12D).
Figure 12B:
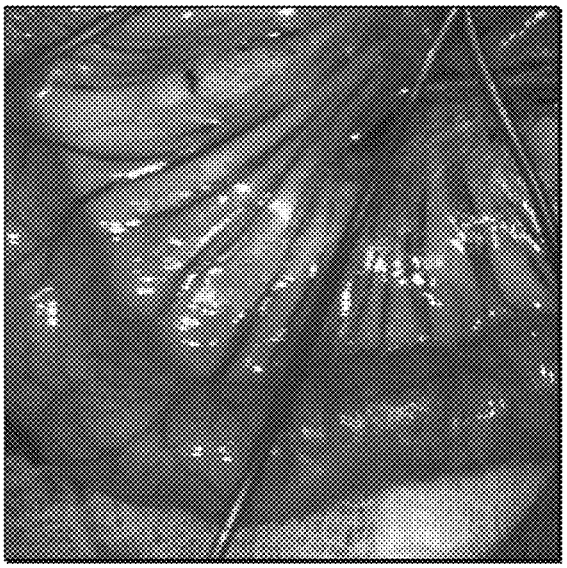
Figure 12C:
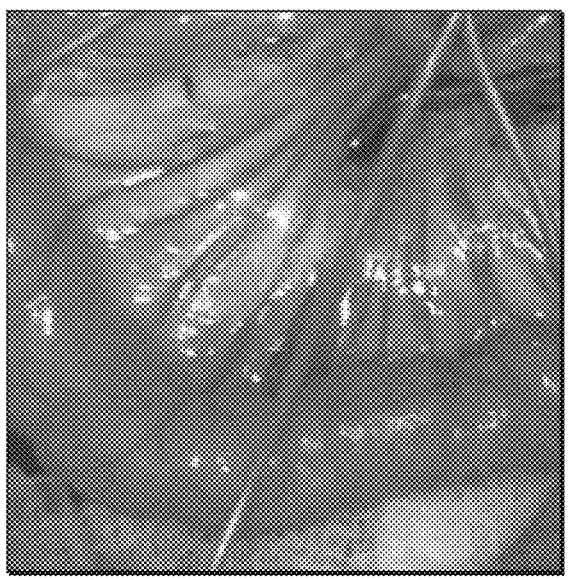
Figure 12D:
Figure 13A:
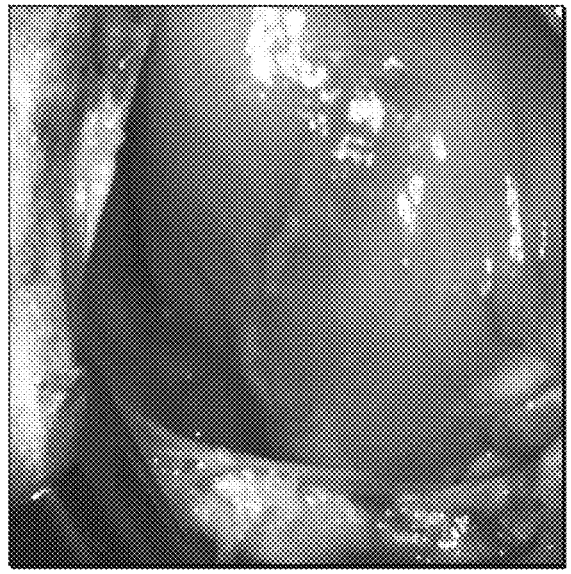
FIGS. 13A-13D are images illustrating Panel A, an NIR 785 nm image of a pig heart (13A); Panel B, Green 532 nm image of the same pig heart (13B); Panel C, a reconstructed image of the same pig heart (13C); and Panel D, an image of the same pig heart taken by a regular camera (13D).
Figure 13B:
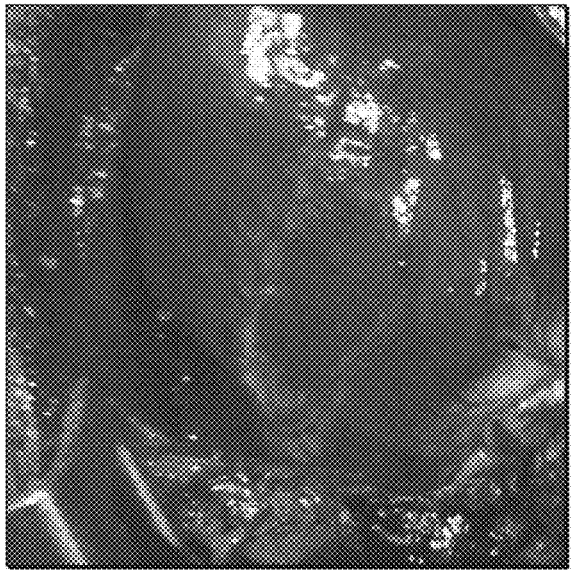
Figure 13C:
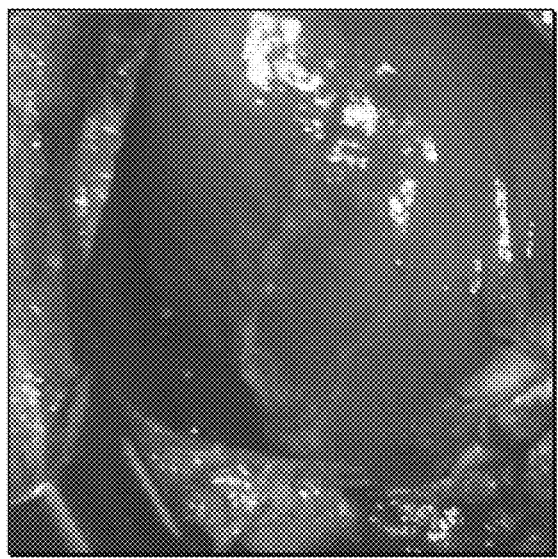
Figure 13D:
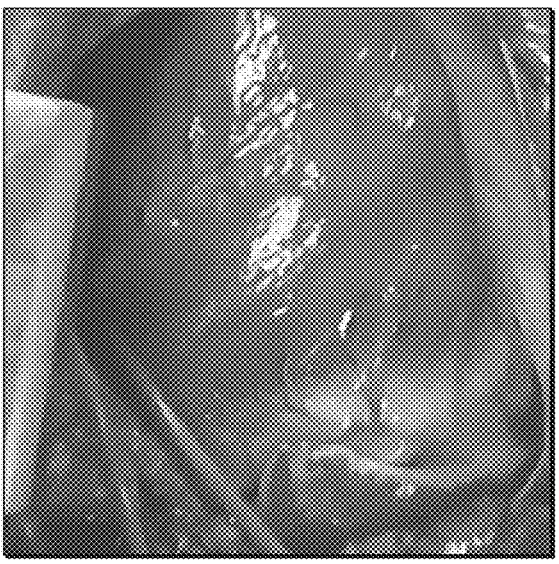

Referring now to FIGS. 13A-13D, images illustrating Panel A, an NIR 785 nm image of a pig heart (13A); Panel B, Green 532 nm image of the same pig heart (13B); Panel C, a reconstructed color image of the same pig heart (13C); and Panel D, an image of the same pig heart taken by a regular camera (13D) will be discussed. FIGS. 13A-13D illustrate using an NIR image as a red color channel and a 532 nm image as a green color channel, the color image of a pig heart can be generated without using a color camera. If the information of one color channel is missing, an algorithm is designed to generate this data using the information of the other two color channels. Since the color of a sample (tissue/organ) is mainly red, embodiments of the present inventive concept can generate color that is very close to the original one as long as the information of the red color channel is available as discussed with respect to FIGS. 10A-10D and 11A-11D. Thus, embodiments of the present inventive concept allow the reconstructed color image to reveal information of deeper tissue/organ if NIR is used as the red color channel as shown in Panel C (FIG. 12C) vs. Panel D (FIG. 12D).

As discussed briefly above with respect to the Figures, some embodiments of the present inventive concept use two wavelengths of differential transmittance through target tissue to apply LSI or LDI. In some embodiments, a first wavelength is within the visible range having zero or very shallow penetration, such as blue light (450-495 nm). The imaging result of this non-penetrating illumination serves as capturing the anatomical structure of tissue/organ surface and position marker of the target tissue/organ, but not the subsurface movement of blood flow and perfusion. A second of the two wavelengths is Near Infra-Red (NIR), which has much deeper penetration and the imaging result of this NIR illumination reveals the underlying blood flow physiology, which correlates both to the motion of the target tissue/organ and also the movement of blood flow and perfusion.

Using the imaging measurement of the visible light as a baseline, the true motion of blood flow and perfusion can be derived from the NIR imaging measurement without being affected by the motion artifact of the target. Furthermore, the anatomical structure information captured by visible light and the physiological characteristics measured by NIR light may be synthesized together according to some embodiments of the present inventive concept. The synthesized imaging product according to embodiments discussed herein provides a previously unattainable clarity of visualization and accuracy of quantification of blood flow and perfusion across the spectrum of clinical applications of laser imaging technologies.

Thus, embodiments of the present inventive concept provide improved image quality and real time data acquisition (several seconds vs. minutes for all other technologies) and analysis. This real time aspect of the present inventive concept makes this technology a real option for sustained adoption of the technology by a surgeon/provider. Embodiments of the present inventive concept accurately depict and quantify blood flow and perfusion.

Further embodiments of the present inventive concept are directed to color image reconstruction using multi-wavelength imaging techniques discussed herein. It will be understood that the images are presented in a gray scale as the patent application publishes in black and white. In particular, using a dual wavelength imaging technique as discussed herein, two images may be acquired simultaneously. One is near infra-red image IR(x,y) and the other is a visible image VIS(x,y). X and Y represent the index of the horizontal and vertical pixel. To reconstruct a red green blue (RGB) color image, red, green and blue channels are calculated separately as follows:

$$R(x, y) = (2^N - 1) \times a_1 \times \left( \frac{NIR(x, y) - \min(NIR(x, y))}{\max(NIR(x, y) - \min(NIR(x, y))} \right)^{b_1} \quad \text{Eqn. (5)}$$

$$G(x, y) = (2^N - 1) \times a_2 \times \left( \frac{VIS(x, y) - \min(VIS(x, y))}{\max(VIS(x, y) - \min(VIS(x, y))} \right)^{b_2} \quad \text{Eqn. (6)}$$

$$B(x, y) = (2^N - 1) \times a_3 \times \left( \frac{VIS(x, y) - \min(VIS(x, y))}{\max(VIS(x, y) - \min(VIS(x, y))} \right)^{b_3} \quad \text{Eqn. (7)}$$

$$\frac{NIR(x, y) - \min(NIR(x, y))}{\max(NIR(x, y) - \min(NIR(x, y))} \quad \text{Eqn. (8)}$$

where R(x,y), G(x,y), B(x,y) are the red, green and blue channels, respectively, of the RGB color image; N is the bit of the color map, for example, 8 bit or 16 bit; a and b are the adjusting parameters for each channel; min is the function to get the minimum value; max is the function to get the maximum value; and Eqn. (8) serves as a normalization of the original image of one specific wavelength. Furthermore, the brightness, contrast and gamma value of the original image of one specific wavelength might be adjusted before applying the equations above.

The multi-wavelength color image recreation technique in accordance with some embodiments of the present inventive concept may reduce the need for an extra color camera in the device; can create a color image with a minimum of two wavelengths; and compared with traditional color images, the color image produced in accordance with embodiments discussed herein visualizes a larger depth of penetration due to use of near infra-red wavelength.

Figure 14A:
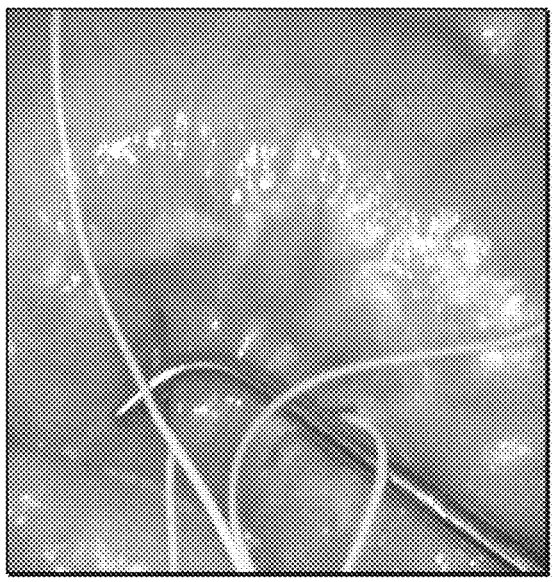
FIGS. 14A-14E illustrate an image using a visible wavelength (532 nm) (14A); an image using near infra-red wavelength (785 nm) (14B); a reconstructed image (in gray scale) with the visible and infrared wavelengths (14C); a regular image with room light illumination (14D); and an image showing blood flow and perfusion image (14E).
Figure 14B:
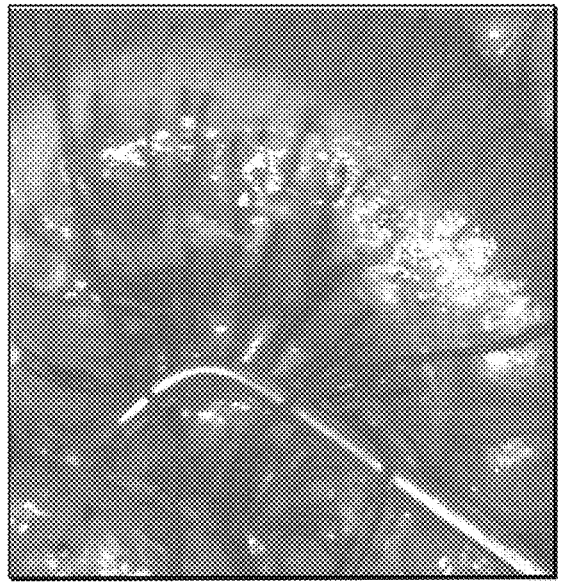
Figure 14C:
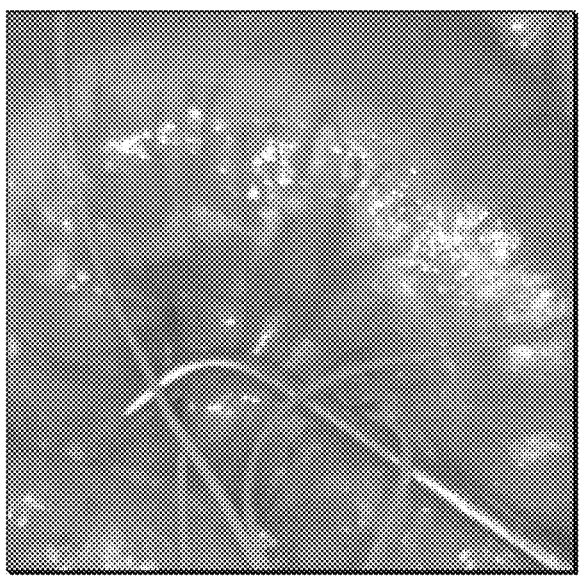
Figure 14D:
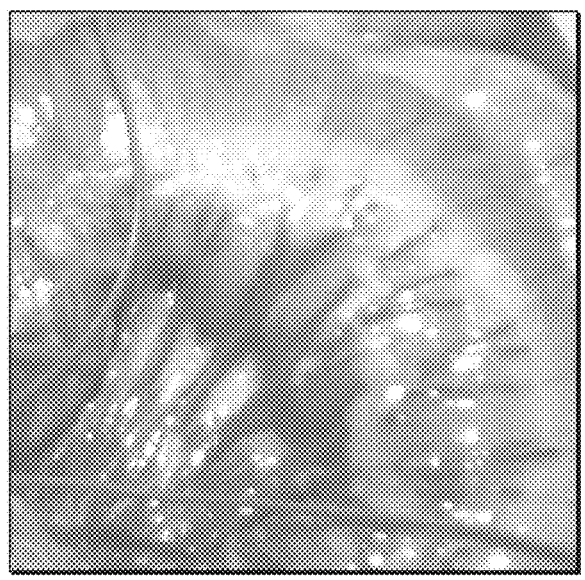
Figure 14E:
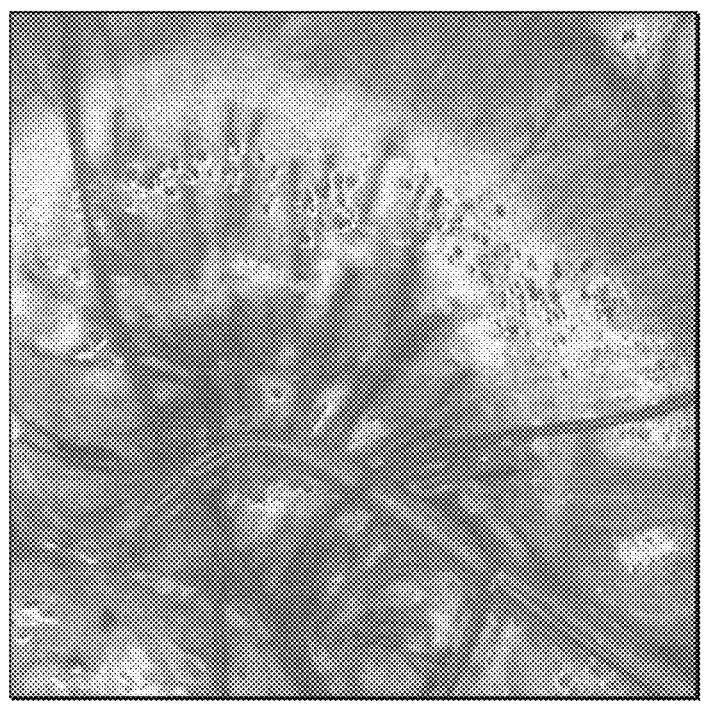

Referring now to FIGS. 14A through 14E, various images of a segment of a large bowel of a pig imaged using the multi-wavelength imaging device in accordance with some embodiments of the present inventive concept will be discussed. FIG. 14A is an image of the bowel of the pig obtained using a visible wavelength (532 nm). FIG. 14B is an image of the bowel of the pig using a near infra-red wavelength (785 nm). FIG. 14C is an image of the bowel of the pig reconstructed with the wavelengths of FIGS. 14A and 14B. FIG. 14D is a regular color image (shown in gray scale) of the bowel with room light illumination. FIG. 14E is a blood flow and perfusion image of the bowel in accordance with some embodiments of the present inventive concept.

Figure 15A:
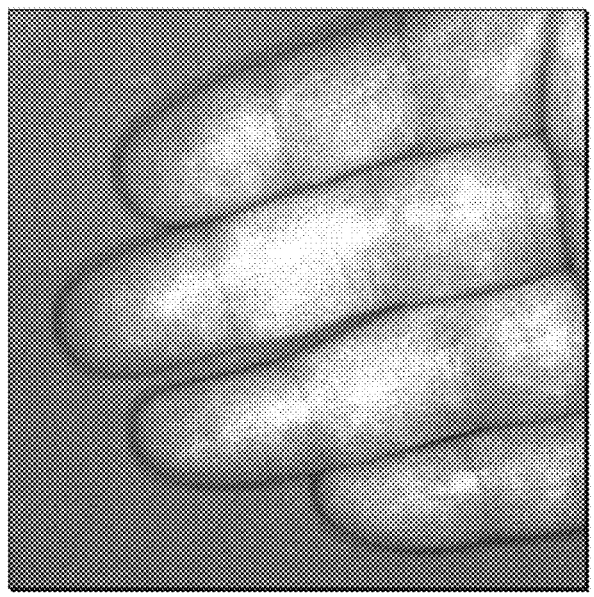
FIGS. 15A-19B illustrate images that compensate for issues during clinical imaging procedures in accordance with some embodiments of the present inventive concept.
Figure 15A:
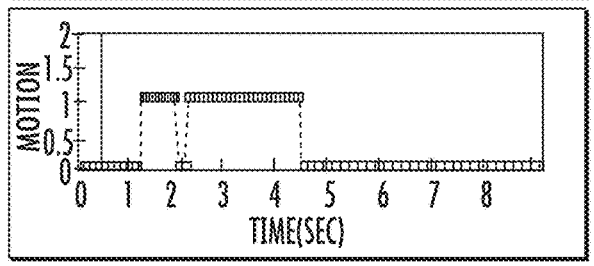
Figure 15B:
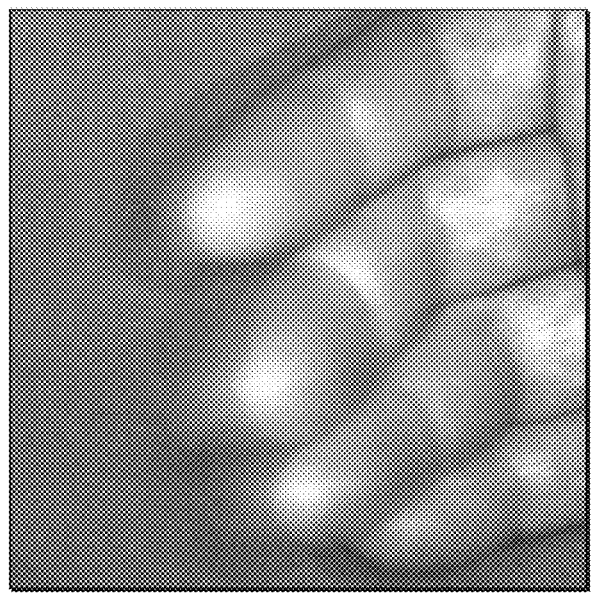
Figure 15B:
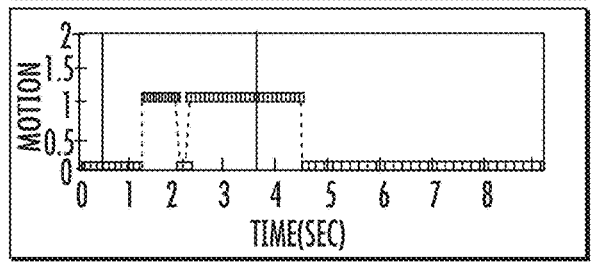

Referring now to FIGS. 15A to 19B, details with respect to real time image quality test protocols will be discussed. Real time image quality test protocols are developed based on customized algorithms using image registration and image metadata to examine the following issues during a clinical imaging procedure:

Movement of target: FIGS. 15A and 15B illustrate images of a stationary hand (15A) and a moving hand (15B) detected by a customized image registration algorithm. By a customized image registration and optical flow algorithm, the quantified detection result curves can be drawn under the images.

Figure 16B:
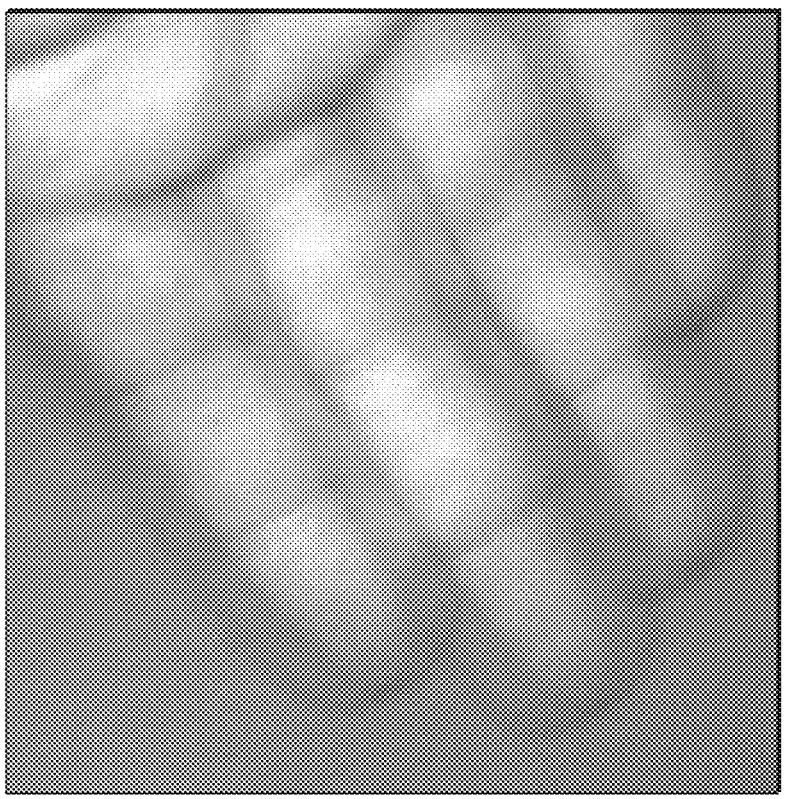
Figure 16B:
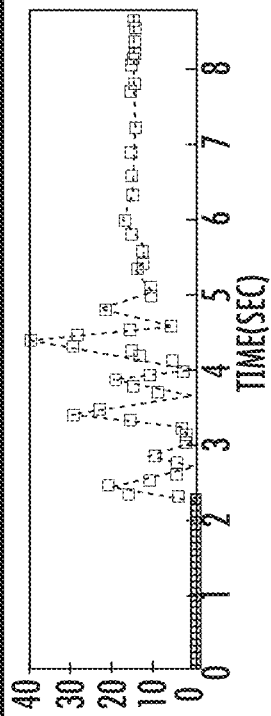
Figure 16A:
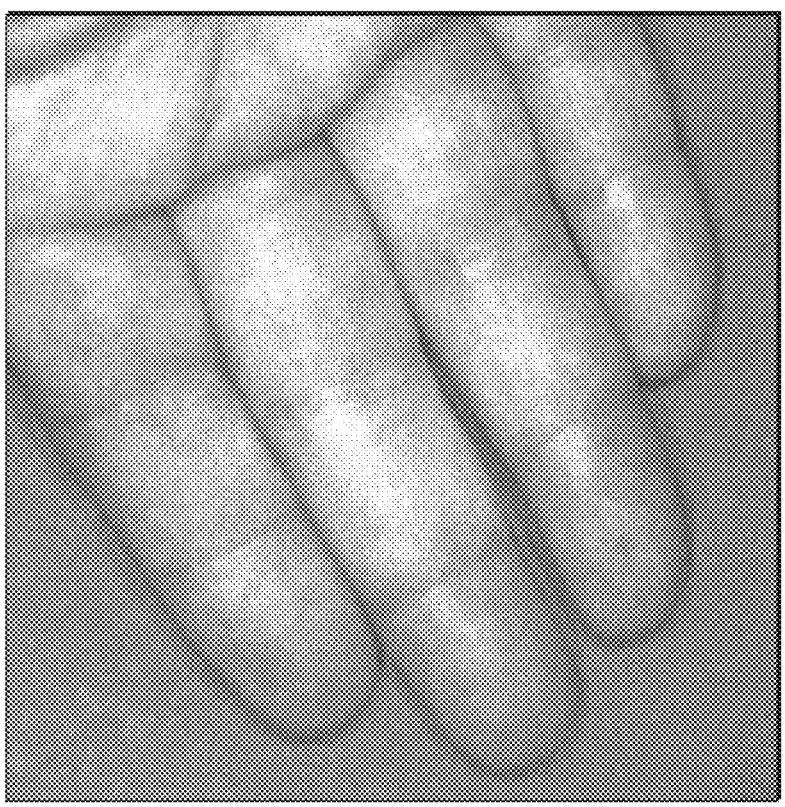
Figure 16A:
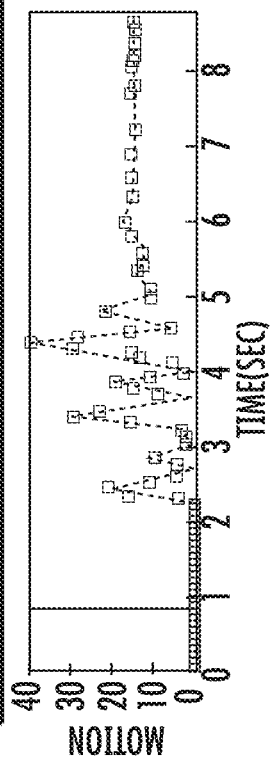

Movement of a field of view or the Camera: FIGS. 16A and 16B illustrate imaging of a hand image captured by stationary camera (16A) and a hand captured by moving camera (16B) detected by customized image registration algorithm.

Figure 17B:
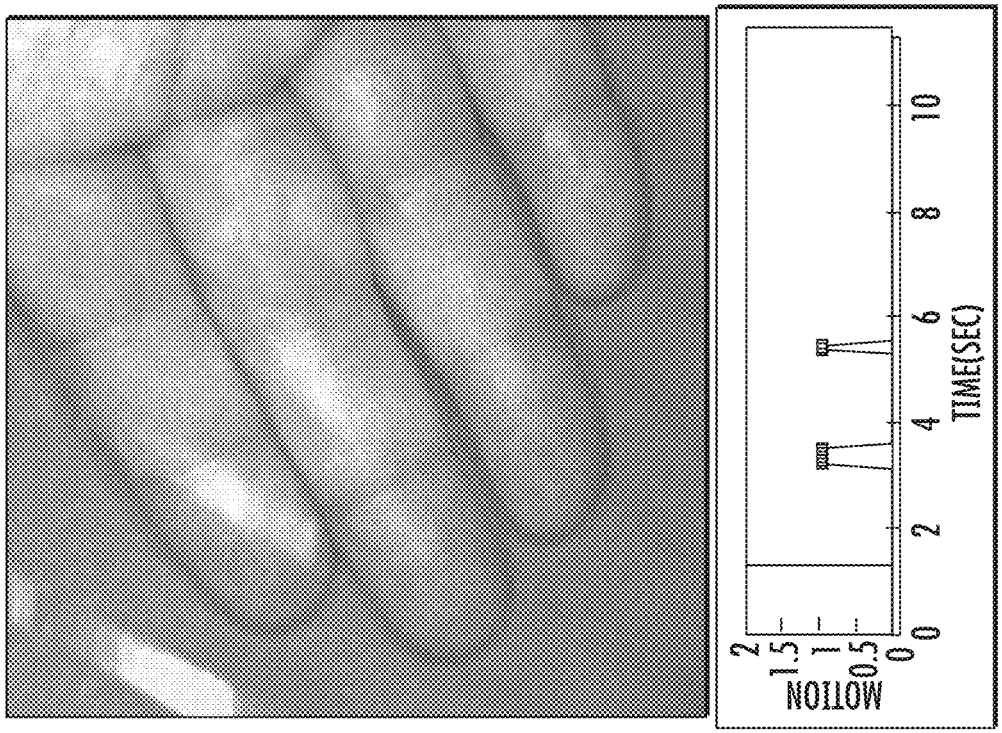
Figure 17A:
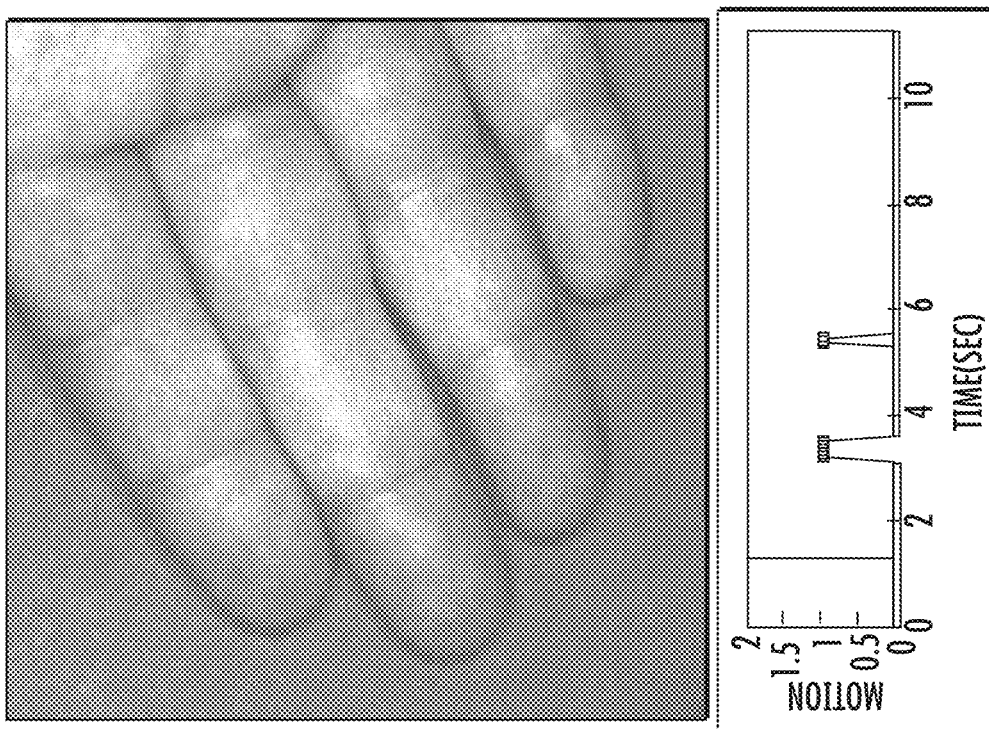

Blocked field of view: FIGS. 17A and 17B illustrate an image of a hand (17A) and an image of a hand that is partially blocked by a twister (17B) and this blocked field of view is detected by a customized image registration algorithm.

Figure 18B:
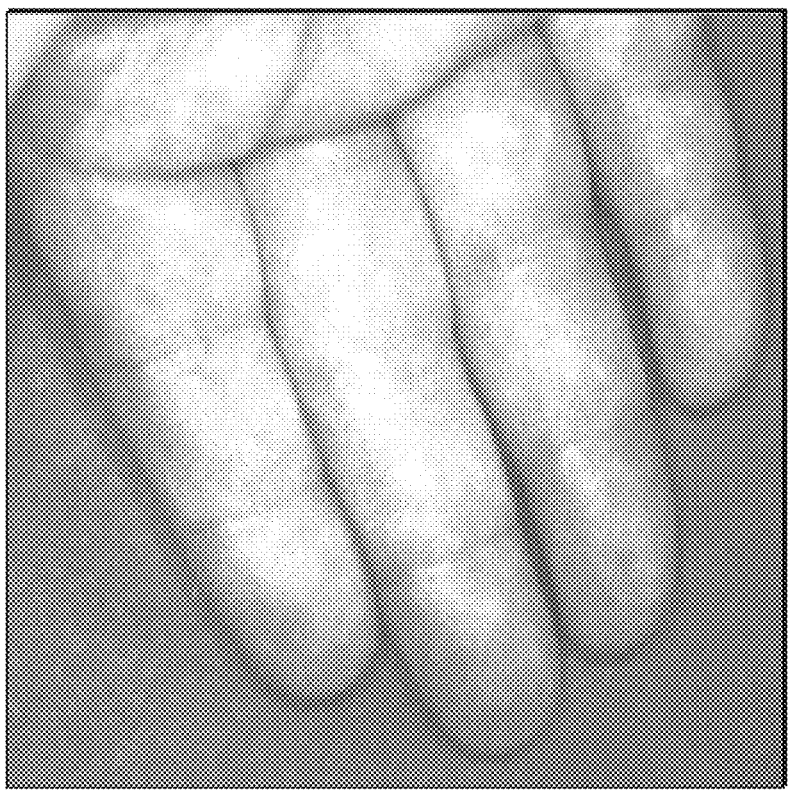
Figure 18B:
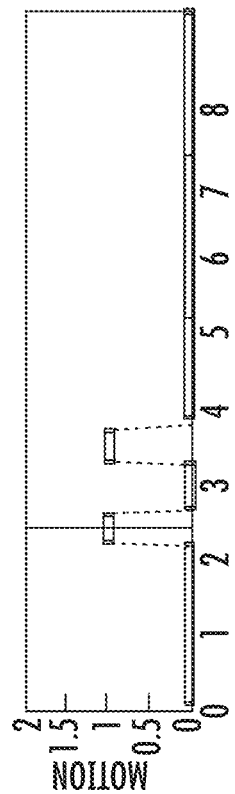
Figure 18A:
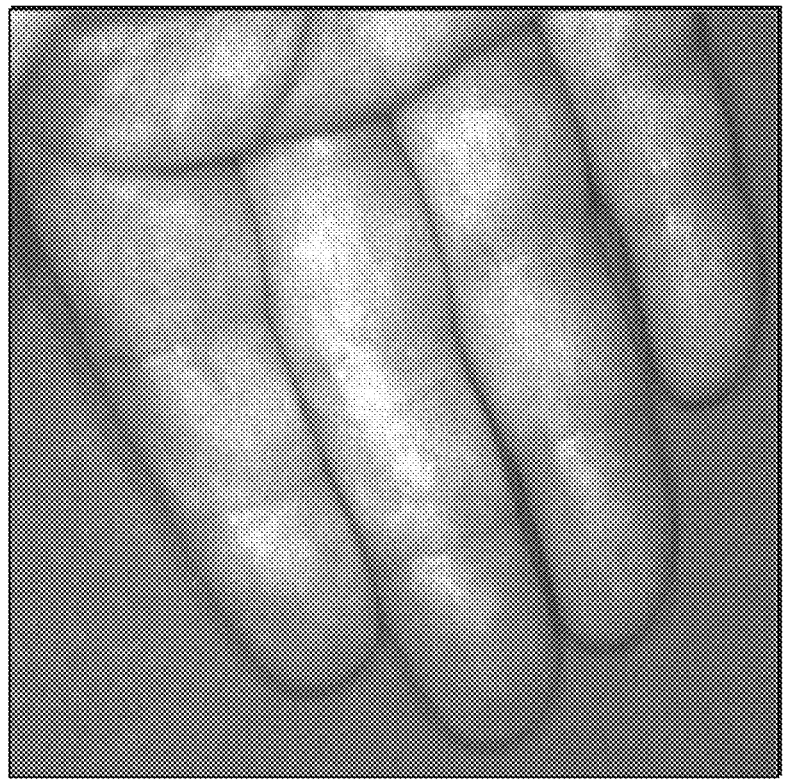
Figure 18A:
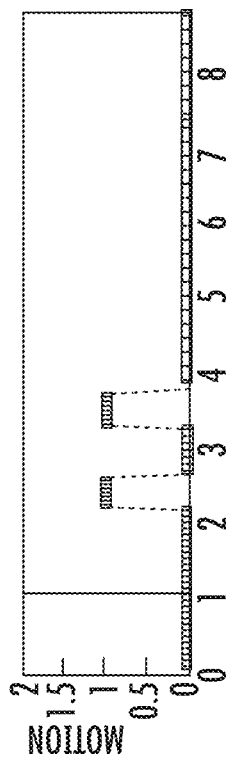

Intrusion of headlight of surgeon/physician: FIGS. 18A and 18B illustrate an image of a hand (18A) and an image of a hand with a head light shining on it (18B) and this extra light within the FOV is detected by a customized algorithm using metadata in the image.

Figure 19B:
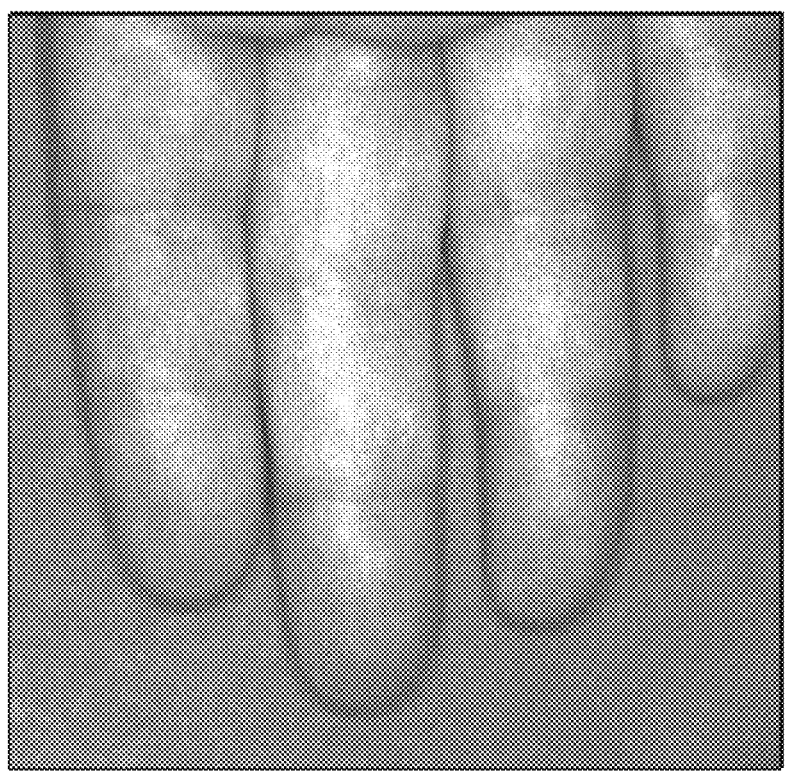
Figure 19B:
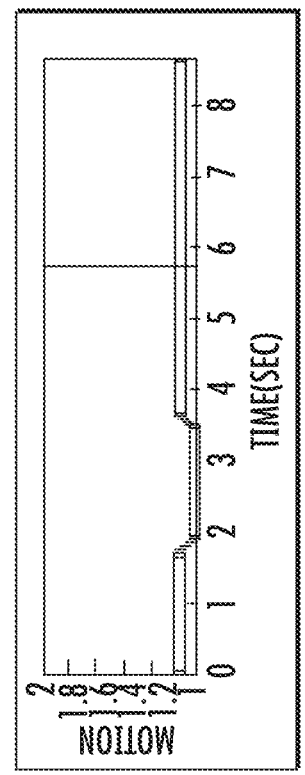
Figure 19A:
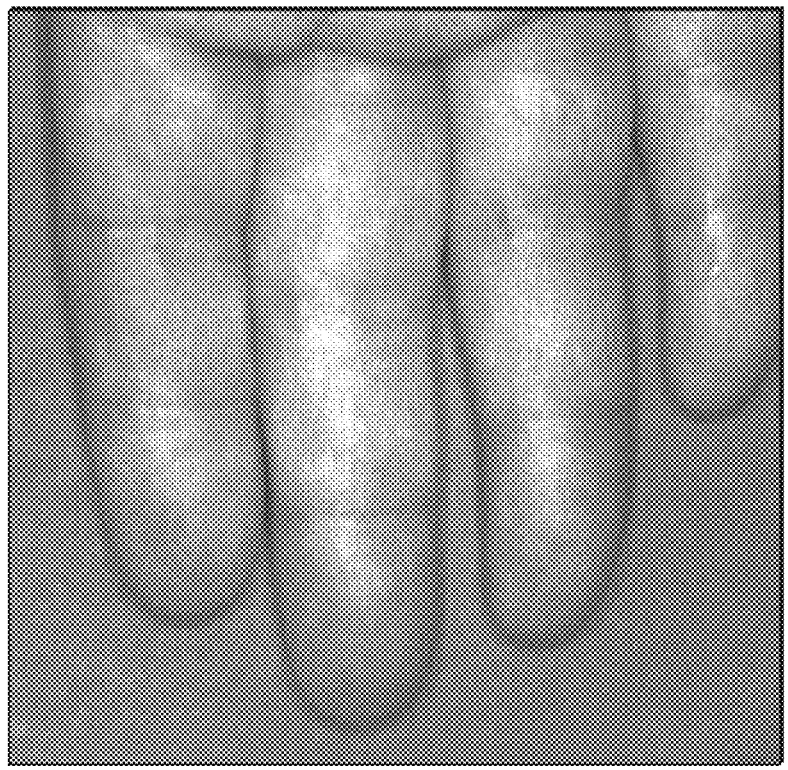
Figure 19A:
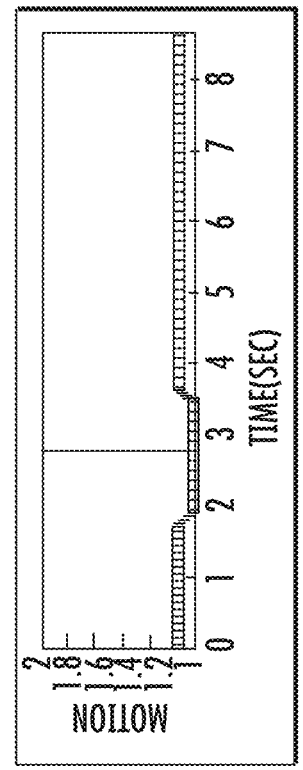

Ambient light condition: FIGS. 19A and 19B illustrate an image of a hand with a room light off (19A) and an image of a hand image with the room light on (19B) and this is detected by customized algorithm using metadata in the image.

The goal of this process is to reduce the likelihood, or possibly eliminate, low quality images caused by incorrect image acquisition to improve the visualization and increase accuracy of the quantification of the blood flow and perfusion imaging in accordance with some embodiments of the present inventive concept.

As discussed above, the data obtained using the imaging methods discussed above can only be used to derive distribution of blood flow speed u. In clinics, the information on distribution of blood flow rate given by the product of blood flow velocity u and the cross section area of blood vessel A is needed. To obtain the distribution of u(r) where r is the three dimensional coordinate, the Navier-Stokes equation has to be solved, which is given by Equations (9) and (10) set out below:

$$\rho \cdot \left( \frac{\partial u}{\partial t} + u \nabla \cdot u \right) = -\nabla p + \mu \cdot \nabla^2 u + F \quad \text{Eqn. (9)}$$

$$\frac{\partial \rho}{\partial t} + \nabla \cdot (\rho u) = 0 \quad \text{Eqn. (10)}$$

where ρ is the density (kg/m3), u is the flow velocity vector (m/s), p is the pressure (N/m2 or Pascal), F is the volume force vector (N/m3) and m is the viscosity. Solving the Navier-Stokes equations produces a velocity field, i.e. a distribution of fluid velocity in space and time. Once this velocity field is obtained, other quantities of interest, such as flow rate and drag force, can be calculated. These calculated quantities can be compared to the experimental data obtained using the methods discussed above to validate the data.

Computational procedures for a non-invasive measurement of blood flow rate distribution in principal vessels in tissues/organs will now be discussed with respect to some embodiments of the present inventive concept. Procedures begin by illuminating a tissue region of interest with a coherent light source, such as a laser with sufficiently long wavelength for relatively large penetration depth between, for example, 550 nm to about 1100 nm as the second wavelength. Using methods discussed above, scattered light at the second wavelength is acquired to determine spatial distribution of blood flow speed in the principal vessels and perfusion distribution in tissue in the region of interest. A velocity field of u(r) for the region of interest is calculated numerically. In some embodiments, the velocity field is calculated using Equations (9) and (10) set out above. Blood flow speed in the region of interest based on the calculated velocity field is calculated. The calculated blood flow speed in the region of interest is compared to the blood flow speed determined using the acquired image data at the second wavelength from the region of interest to verify results.

Referring now to FIGS. 20A through 21B, embodiments for using MSLI discussed above with respect to FIGS. 1A through 19 to determine peripheral oxygen saturation ($SpO_2$) will be discussed. In particular, embodiments of the present inventive concept illustrate a correlation between image intensity and an $SpO_2$ value as will be discussed further below.

$SpO_2$ is a percentage of oxygenated hemoglobin relative to a total amount of hemoglobin found in the bloodstream. The $SpO_2$ determination is used clinically as a monitoring technique to determine if a patient has a sufficient level of oxygen at any given time. The quantitative value represents the relative performance of the cardiovascular system in supplying oxygen throughout the body. This assessment is important in the detection of hypoxemia, or abnormal decrease in oxygen content, in patients. Conventional techniques for determining $SpO_2$ use pulse-oximeter devices that generally require patient contact, which is classified as an invasive technique. Non-contact and completely non-invasive techniques for monitoring of blood oxygen saturation have also been attempted, however, improvement for non-contact and non-invasive techniques are desired. Some embodiments of the present inventive concept provide such a technique, as will be discussed further herein.

In particular, to determine $SpO_2$, the Beer-Lambert law is used to linearly correlate $SpO_2$ to the ratio-of-ratios (RR) signal. The Beer-Lambert law generally states that the quantity of light absorbed by a substance dissolved in a fully transmitting solvent is directly proportional to the concentration of the substance and the path length of the light through the solution. The RR signal is determined using the ratio of pulsatile signals (AC) to non-pulsatile signals (DC) from two different wavelengths. One wavelength is used to represent the amount of oxygenated hemoglobin, while the other is used to represent the amount of total hemoglobin in the bloodstream. The AC and DC components are taken from the two independent signals to calculate an R ratio for each. The R ratios of both wavelengths are then compared to determine an RR signal, which is finally correlated to an $SpO_2$ percentage. The mathematical determination can be defined using the equations below. In particular. $SpO_2$ is determined by the amount of oxygenated hemoglobin relative to total hemoglobin as follows:

$$SpO_2 = \frac{[HbO_2]}{[HbO_2][Hb]} * 100 \qquad \text{Eqn. (11)}$$

wherein $SpO_2$ is percentage of oxygenated saturation in arterial blood; HbO2 is the concentration of oxygenated hemoglobin measured in blood; and Hb is the concentration of hemoglobin in blood. As illustrated in Eqn. (12) below, $SpO_2$ is linearly related to the RR signal by the Beer-Lambert law.

$$SpO_2 = m*RR + b \qquad \text{Eqn. (12)}$$

where m is the correlation coefficient between the RR signal intensity and $SpO_2$ percentage; RR is the ratio of pulsatile signals (AC) to non-pulsatile signals (DC) from two different wavelengths and is a measure of the signal intensity, and b is the y-intercept of the trend line of the relation between RR intensity and $SpO_2$ percentage.

The RR signal is calculated as the ratio of pulsatile signals to non-pulsatile signals from two different wavelengths as follows:

$$RR = \frac{R_{\lambda 1}}{R_{\lambda 2}} = \frac{\frac{AC_{\lambda 1}}{DC_{\lambda 1}}}{\frac{AC_{\lambda 2}}{DC_{\lambda 2}}} \qquad \text{Eqn.(13)}$$

where $AC\lambda 1$ is a pulsatile signal at a first wavelength and $DC\lambda 1$ is a non-pulsatile signal at the first wavelength; and $AC\lambda 2$ is a pulsatile signal at a second wavelength and $DC\lambda 2$ is a non-pulsatile signal at the second wavelength.

A noncontact imaging technology exists that combines visible and near-infrared wavelengths of light to monitor oxygen saturation ($SpO_2$). The imaging system for this technology consists of one camera with two identical light emitting diode (LED) arrays placed on each side of the system. The LED arrays include alternating rows of the visible and near-infrared wavelengths, and each row is timed to switch on and off alternatively so that the imaging data from each wavelength would be equal in size. From the imaging data, a region of interest (ROI) is selected to provide a photoplethsymography (PPG) signal to be used in the $SpO_2$ calculation. For both wavelengths, the image intensity is averaged over all the pixels in that ROI to determine the PPG signal used. The AC and DC components are extracted from the PPG signal by calculating the average peak-to-peak and mean values respectively. These two variables are used as the AC (peak-to-peak) and DC (mean) values for the individual wavelength ratio calculation ($R_{\lambda 1}$, $R_{\lambda 2}$) shown in the Eqn. (14) set out below. With the two ratios known, the ratio-of-ratios (RR) value is then calculated to correlate with an $SpO_2$ percentage.

$$RR \text{ Signal} = \frac{R_{\lambda 1}}{R_{\lambda 2}} = \frac{\frac{AC_{\lambda 1}}{DC_{\lambda 1}}}{\frac{AC_{\lambda 2}}{DC_{\lambda 2}}} = \frac{\frac{\text{Peak-to-Peak}_{\lambda 1}}{\text{Mean}_{\lambda 1}}}{\frac{\text{Peak-to-Peak}_{\lambda 2}}{\text{Mean}_{\lambda 2}}}, \qquad \text{Eqn. (14)}$$

$$\lambda 1 = VIS, \lambda 2 = NIR$$

where the first wavelength is a visible wavelength and the second wavelength is near infrared.

In stark contrast to using a one-dimensional PPG signal that uses the intensity of the imaging data, embodiments of the present inventive concept provide a noncontact imaging routine to calculate $SpO_2$ using two-dimensional imaging data to provide the AC and DC components that makeup the individual ratios of both wavelengths.

It will be understood that ideally optimal visible and near-infrared wavelengths would be identified along with the hardware configuration. However, for purposes discussed herein, standard deviation (STD) and mean of the image data are used for the RR value equation shown below. The standard deviation (STD) and mean values used are two-dimensional arrays to represent the STD and mean of the image set, while conventional methods discussed above rely on one-dimensional values of an intensity signal. Accordingly, the RR value is replaced with an RR image. The intensity of a ROI from that RR image is then correlated to the $SpO_2$ percentage. Thus, embodiments of the present inventive concept illustrate a new way of evaluating $SpO_2$ in addition to the traditional $SpO_2$ determination.

$$RR \text{ Image} = \frac{R_{\lambda 1}}{R_{\lambda 2}} = \frac{\frac{AC_{\lambda 1}}{DC_{\lambda 1}}}{\frac{AC_{\lambda 2}}{DC_{\lambda 2}}} = \frac{\frac{STD_{\lambda 1}}{Mean_{\lambda 1}}}{\frac{STD_{\lambda 2}}{Mean_{\lambda 2}}}, \quad \text{Eqn. (15)}$$

$$\lambda 1 = VIS, \lambda 2 = NIR$$

Some embodiments of the present inventive concept illustrate that MSLI which is also known as Multi-Spectral Physiologic Visualization (MSPV) technology can be used to relate peripheral oxygen saturation in the target tissue to the RR image intensity. Experiments illustrating embodiments of the present inventive concept have been performed. In particular, in a first test two different laser diodes with different wavelengths were used, one at 690 nm to represent the visible (VIS) wavelength in the RR image calculation and one at 785 nm to represent the near-infrared (NIR) wavelength in the RR image calculation. It will be understood that although the current interchangeable laser diode system produces a power level of 12 mW for the 690 nm laser diode, embodiments of the present inventive concept are not limited to this configuration. Furthermore, the 785 nm laser power was decreased to this low power level to match the surface intensity of both wavelengths to reduce any signal interference. Furthermore, these additional wavelengths can be one or more of the first and second light sources or may be the third or fourth light sources. An MSPV prototype system was used to capture ten (10) seconds of imaging data at each wavelength under different experimental conditions. The results of these experiments are discussed below with respect to FIGS. 20 and 21.

Figure 20A:
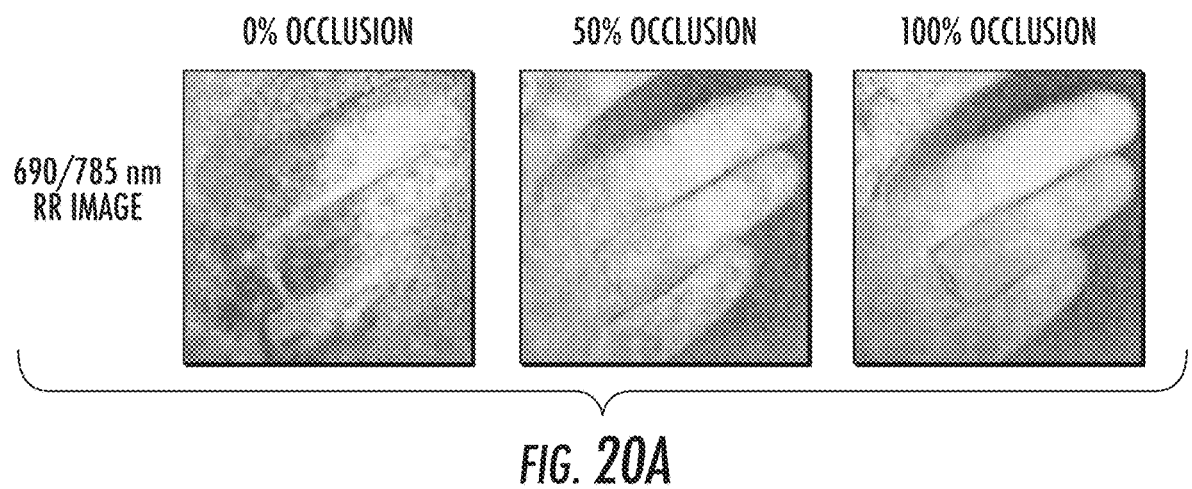
FIGS. 20A through 20C illustrate MSPV images at each wavelength combination and occlusion level in accordance with some embodiments of the present inventive concept.
Figure 20B:
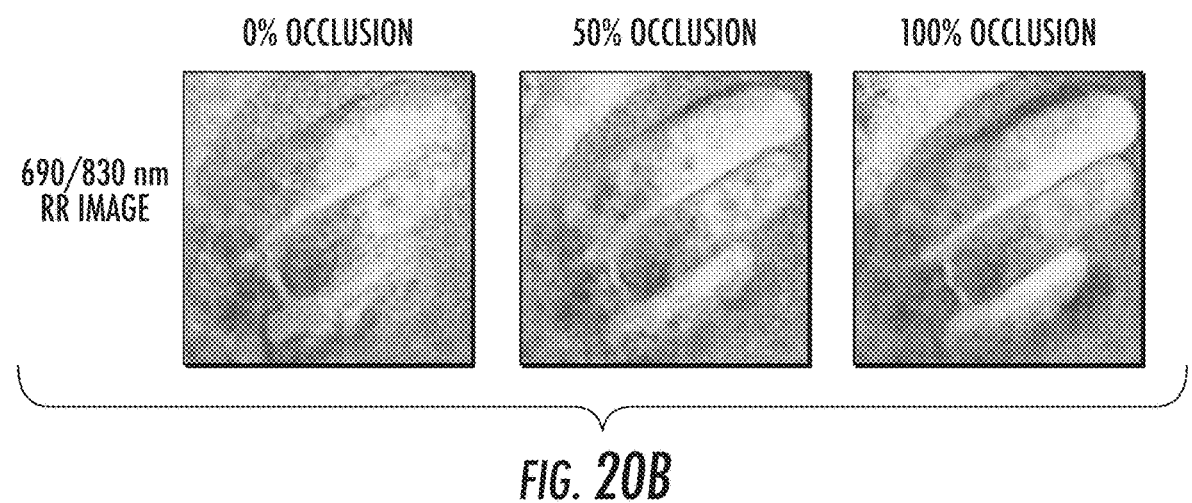
Figure 20C:
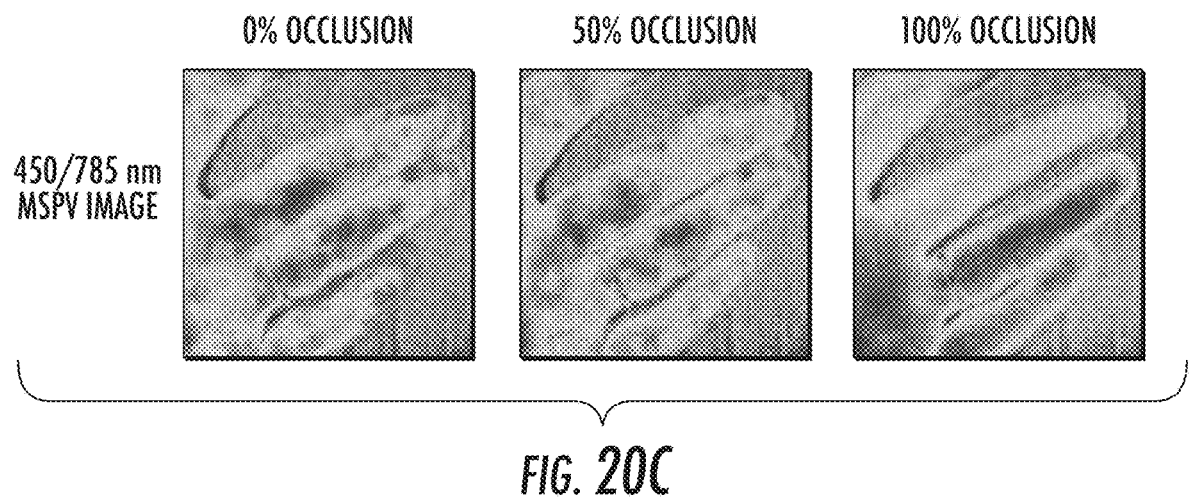

During a first experiment, three different wavelengths were used to test embodiments for correlating the RR image signal to $SpO_2$ value measured with a pulse-oximeter. The combination of wavelengths tested include 690 nm+785 nm and 690 nm+830 nm lasers. However, embodiments of the present inventive concept are not limited thereto. Any type of light sources may be used without departing from the scope of the present inventive concept. During the experiment, a conventional pulse-oximeter was attached to the index finger of the left hand, and this hand was placed under the field of view (FOV) for imaging. A blood pressure cuff was used to decrease the blood supply to the left arm at certain pressure values ranging from baseline, to intermediate, to maximum occlusion levels. These values were determined to be 0 mmHg, 110 mmHg, and 170 mmHg (occlusion levels 1, 2 and 3, respectively) to cause a decrease in the $SpO_2$ value calculated with the pulse oximeter. In some embodiments, a subject under test could be instructed to hold their breath, which would reduce oxygen without reducing blood flow. Each of the three wavelength was imaged separately at all three occlusion levels and the near-infrared imaging data was collected from the iCertainty prototype device to be used in subsequent calculations. The $SpO_2$ value was found to drop from an average of 98% to 97% to 91% at each of the 1, 2, and 3 occlusion levels, respectively. One second of data (generally includes about 163 frames due to high frame rate) was selected for calculation of an RR image from the two wavelength combinations, along with the MSPV image using only the 785 nm imaging data to show the change in blood supply/perfusion to the left hand at each imaging sequence. Imaging results for the first experiment are illustrated in FIGS. 20A through 20C. In particular, FIGS. 20A through 20C illustrates 0 percent, 50 percent and 100 percent occlusion at all three wavelength combinations, 690/785 nm RR images, 690/830 nm RR images, and 450/785 nm, respectively. As illustrated, monitoring the ring finger of the left hand in the RR images shows that the image intensity and the $SpO_2$ value decreases as the cuff pressure increases during the experiment. The MSPV image data also demonstrates the effects of the cuff pressure to occlude the blood supply to the left hand.

It will be understood that since each wavelength data sequence captured was at different time points, and not simultaneously, the left hand may have and, likely did, change position between recordings. The change in the hand position caused a misalignment between the imaging data that led to a determination of an RR signal at areas where the hand was aligned and produced some unwanted noise in areas where there was a misalignment. Due to this constraint, a tissue-oxygen image map could not be produced in this experiment; therefore, a region of interest (ROI) was selected for intensity comparison. In every sequence, the entire ring finger was found to have the best alignment to produce comparative results. The mean of the RR image intensity of the ROI was compared from baseline to 100% occlusion as this represents the highest drop in $SpO_2$ level. For the 690/785 nm data set, the percent difference in intensity from an average drop in $SpO_2$ from 98% to 91% was found to be 10%. In the 690/830 nm data set, the percent difference in intensity from the same $SpO_2$ drop of 98% to 91% was found to be 15%. Both results show that as the $SpO_2$ value decreases the RR image intensity also decreases. However, the only issue with this experiment is that the MSPV results show a loss of perfusion at the drop in $SpO_2$ level.

Figure 21A:
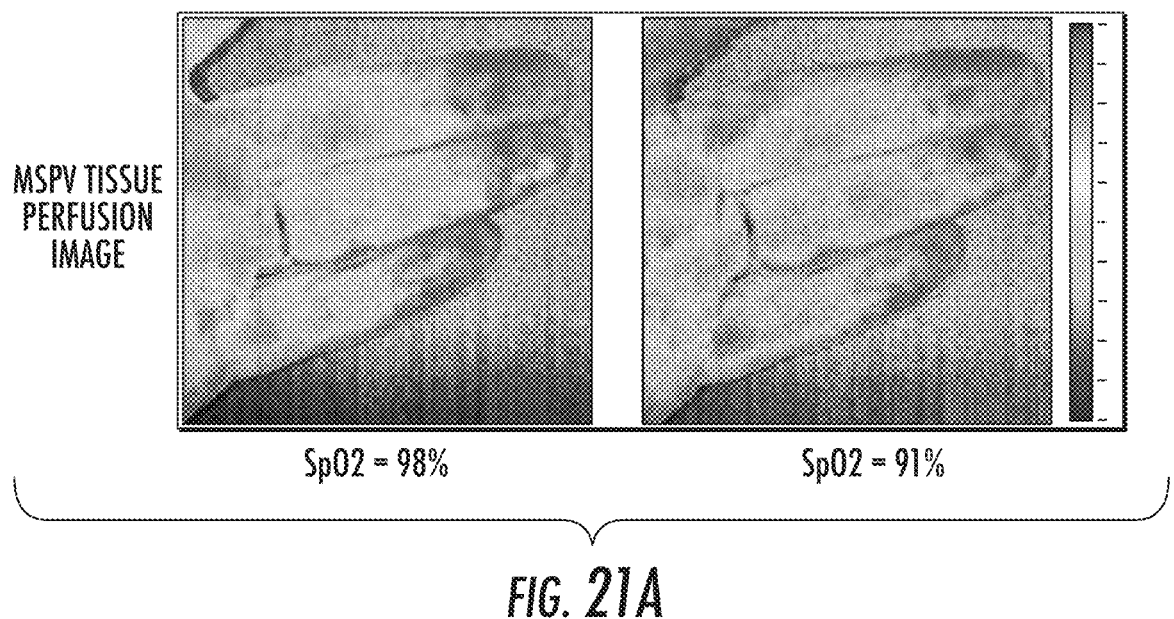
FIGS. 21A and 21B illustrate MSPV and RR images at each $SpO_2$ measurement in accordance with some embodiments of the present inventive concept.
Figure 21B:
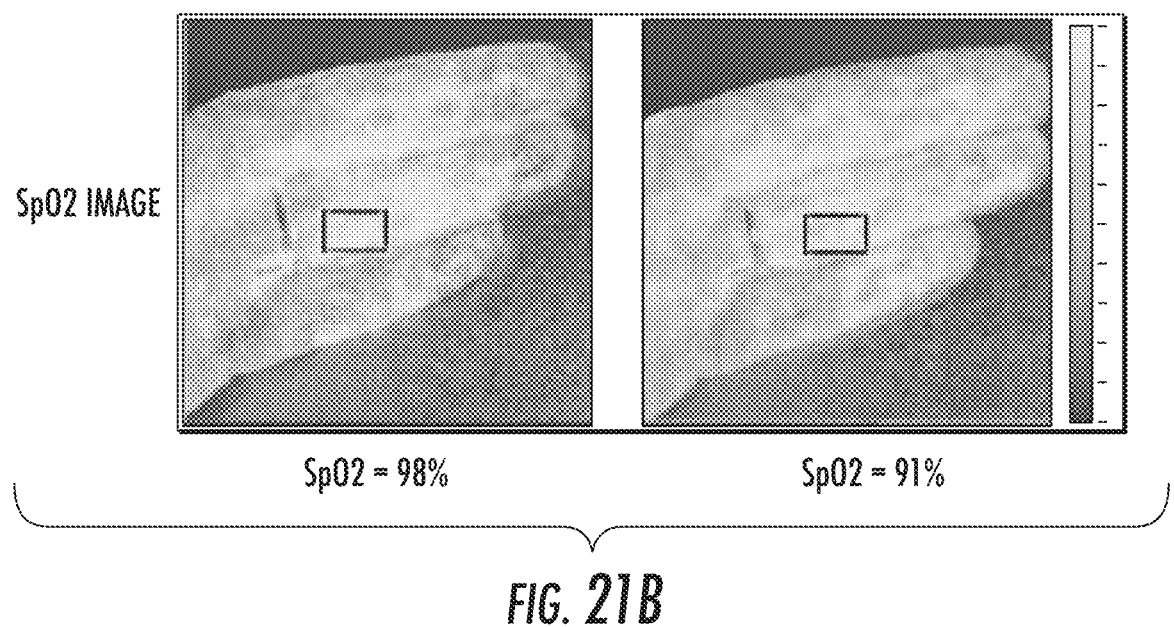

During a second experiment, only one of the wavelength combinations was used. The 690 nm+785 nm lasers were setup to the same low power specifications from the first experiment. The second experiment also followed the same imaging setup of the left hand with the pulse-oximeter placed on the left index finger. The cuff pressure for this experiment was set to 110 mm Hg to allow for a decrease in flow/perfusion and to reduce a possibility of a loss in blood supply to the left hand. Re-breathing was also performed to decrease the peripheral oxygen saturation levels in the hand. These two manipulations in combination caused a decrease in the $SpO_2$ value from a baseline of 98% to 91%, while maintaining the blood supply and MSPV results in the left hand. Baseline and manipulation image sequences were acquired for the 690 nm and 785 nm wavelengths to be used in the RR image calculation. The imaging results show a decrease in the RR image intensity as the $SpO_2$ measure decreases. The same misalignment issues from experiment one were also present in these imaging results and produce some unwanted signal noise. To account for this, a small ROI was selected at the base of the ring finger as there appears to be some misalignment at the tip of the same finger. The percent difference in intensity of the square region of interest (show in FIG. 21B) from a drop in $SpO_2$ of 98% to 91% was found to be 9% in the second experiment. The imaging results from this experiment are illustrated in FIGS. 21A and 21B. As illustrated, the imaging results show no change in MSPV or blood flow/tissue perfusion to the hand image during the peripheral oxygen saturation decrease. The selection of an ROI is not a requirement, however, when the signals are aligned and the full Field of View of the MPSV image can be used for determination of $SpO_2$.

As discussed briefly above, some embodiments of the present inventive concept provide a new approach to the non-contact peripheral oxygen saturation ($SpO_2$) determination. Preliminary results suggest that there is a linear correlation between the RR image intensity and $SpO_2$ change. There were multiple design constraints determined from these experiments, and these constraints will be addressed for future devices. The low power laser diode system used, the misalignment of the hand images, different image acquisition times, and wavelength selection constraints will all be addressed during design and build of the actual device(s). In some embodiments, the low power laser diodes may be replaced by different wavelength LED's to increase the signal-to-noise ratio of the imaging results and provide substantial power and illumination to the field of view. The misalignment caused by different image acquisition times may also be addressed with simultaneous signal capture in real time. Wavelength combination may also be optimized to provide the best correlation of the RR image intensity and $SpO_2$ value at levels ranging from 100% to 80%. This development may be incorporated with the current MSPV solution by the addition of an LED ring to not interfere with the MSPV determination. The LED ring may contain both optimized wavelengths and the subsequent RR image data collection may follow the MSPV determination. Both imaging results may then be calculated and presented to the operator.

In some embodiments, the RR image calculation may also be investigated further to determine a way to calculate a relative hemoglobin ([Hb]) concentration. The lower wavelength will have optical absorption properties—high Hb absorbance and low HbO2 absorbance—and vice versa for the higher wavelength. The [Hb] and [HbO2] can be determined from the absorbance data, and a relative trend of hemoglobin concentration [Hb] can be determined from the relative absorbance changes and the sum of [Hb]+[HbO2]. The tissue oxygen image along with a representation of the relative hemoglobin concentration in the target tissue may provide new data captured alongside the MSPV solution to improve clinical examination of the target tissue imaged.

Furthermore, in some embodiments of the present inventive concept a non-invasive, non-contact peripheral oxygen saturation determination ($SpO_2$), an index of the physiologic endpoint of perfusion, and derived hemoglobin concentration [Hgb] as an index of anemia is provided. $SpO_2$ monitoring is closely associated with hypoxemia, where arterial oxygen tension is below "normal" values, but is unassociated with hypoxia, which is the failure of oxygenation at the tissue level producing anaerobic metabolism. Hypoxemia and hypoxia can be differentiated in part by simultaneously knowing the perfusion status to the tissues and/or the oxygen carrying capacity in the blood. A rise in $SpO_2$ from 88% to 92% increases the oxygen content in the blood by 4%. In contrast, increasing [Hgb] from 8 g/l to 12 g/l increases the oxygen carrying capacity by 33%, and doubling the cardiac output in this situation increases oxygen delivery to tissues by over 60% without any change in $SpO_2$. Thus, knowing all three components ($SpO_2$, [Hgb], and perfusion status) of peripheral oxygen delivery is highly desirable for monitoring—hence the value-added of augmenting MPSV with $SpO_2$ as discussed above, rather than a conventional stand-alone determination of only $SpO_2$.

In some embodiments, two separate wavelengths may be used, the first wavelength having a range of 600-700 nm, and the second wavelength having a range of 800 nm and above according to the absorption spectra of hemoglobin and oxygenated hemoglobin molecules. The illumination source in these embodiments may use multiple LED's of substantial power to provide a uniform intensity onto the FOV, which is set at 9 cm×9 cm at a distance of 32 cm from the target in some embodiments. The $SpO_2$ solution must generally be small enough to not interfere with the standard hardware setup for the MSPV solution. In other words, the wavelengths used to obtain the MSPV data may interfere with the wavelengths used to obtain the oxygenation parameters. Thus, in some embodiments, the light sources may be turned on and/or off in intervals so that both sets of data can be obtained without interference.

Figure 22:
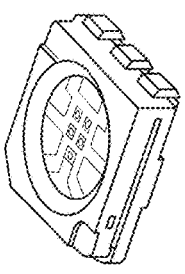
FIG. 22 is a table illustrating various options for illumination devices in accordance with some embodiments of the present inventive concept.
Figure 22:
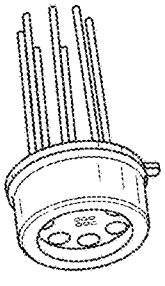
Figure 22:
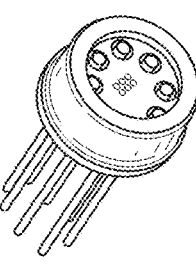
Figure 22:
Figure 22:
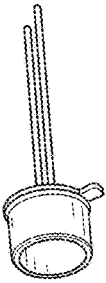

In these embodiments, the illumination sources (light sources) may take on various combinations. Two embodiments will be discussed herein, but embodiments of the present inventive concept are not limited thereto. In the first embodiment, multi-wavelength emitters may be used. Since embodiments of the present inventive concept use two separate wavelengths, the ability to house multiple wavelengths within one emitter solution allows for double the amount of individual LEDs to be used. These embodiments also provide an adjustment in wavelength on the higher end if needed. The disadvantage that may occur with these embodiments is a price increase. The multi-wavelength design options include varying wavelengths of 670 nm, 770 nm, 810 nm, 850 nm, 950 nm, and 1300 nm even though the 950 and 1300 nm options will not be needed. Table 1 set out in FIG. 22 provided various Martech illumination sources that contain multi-wavelength options that may be used in accordance with embodiments discussed herein. However, embodiments of the present inventive concept are not limited to this configuration.

In the second embodiment, the number of available LEDs is divided in half, where one half will supply the first wavelength, and the other half will supply the second wavelength within the system. The advantage of this embodiments is the decrease in price per unit of LEDs and a simpler electronic design. The disadvantage may be increased demand for a greater number of LEDs to provide enough illumination to the target. The LED solutions available from the supplier vary greatly over visible and NIR wavelength, and could include a 670 nm and anywhere from 770 nm-980 nm.

In some embodiments, an electronic circuit board is designed to power the LED array. The electronics may be provided in a housing structure to allow for ease of implementation into the prototype device. The circuit design for a control board of this LED array.

Referring now to FIG. 23, a block diagram of an LED design in accordance with some embodiments of the present inventive concept will be discussed. These LEDs may be incorporated into embodiments of the present inventive concept to replace an existing LED illumination ring with a $SpO_2$ illumination source.

Figure 23B:
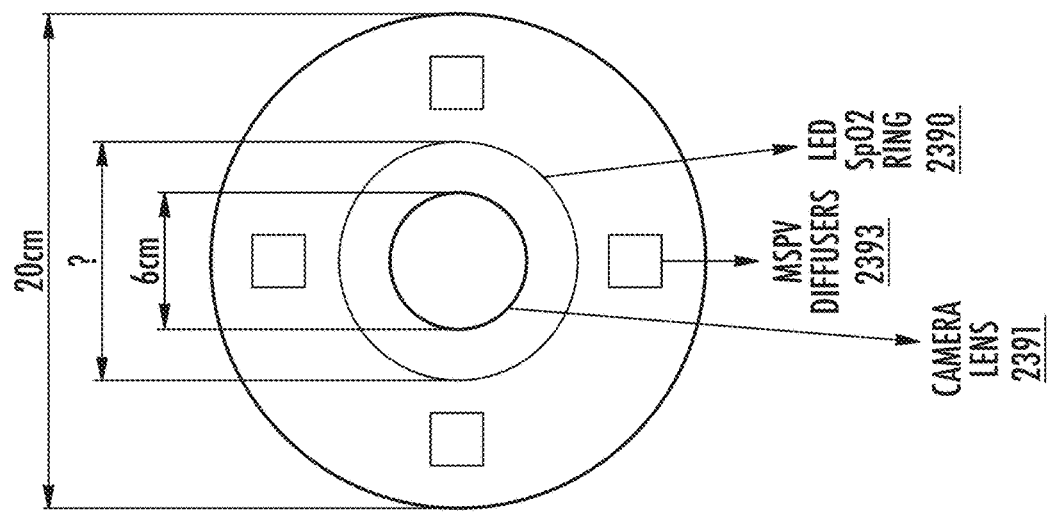
FIG. 23 is a block diagram of a light emitting diode (LED) $SpO_2$ ring design in accordance with some embodiments of the present inventive concept.
Figure 23A:
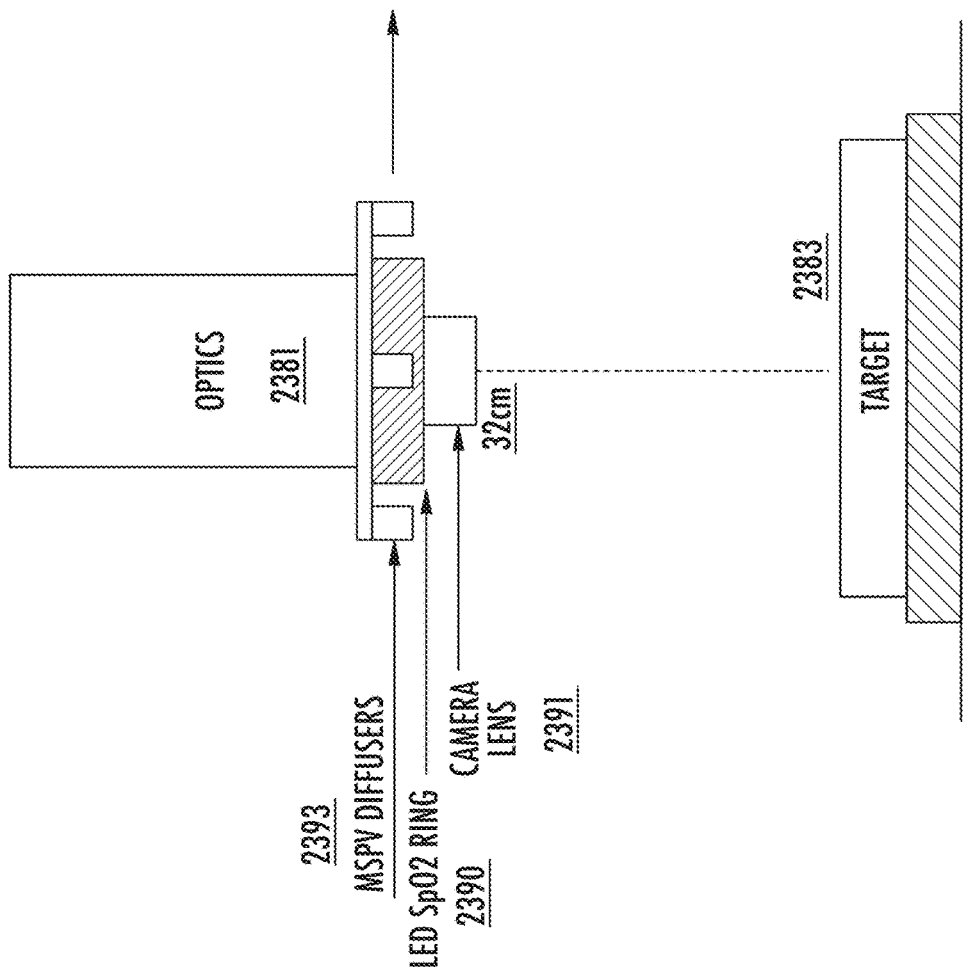

Referring now to FIGS. 23A and 23B, a system for illumination (23A) and a top view thereof (23B) illustrating an LED $SpO_2$ ring design in accordance with some embodiments of the present inventive concept will be discussed. As illustrated, the system in included optics 2381, MSPV diffusers 2393, an LED $SpO_2$ ring 2390, a camera lens 2391 and a target 2383. As illustrated, the LED $SpO_2$ ring 2390 is placed in between the camera lens 2391 and optical diffusers 2393 that are already set in place. Various measurements are illustrated on FIG. 23, however, embodiments of the present inventive concept are not limited thereto.

As discussed above, imaging at the various MSPV wavelengths may interfere with imaging at the $SpO_2$ wavelengths. Thus, the lights sources may be turned on and/or off at various intervals to allow both features to operate without interference. It will be understood that timing and synchronization of image acquisition using the various wavelengths may vary depending on the system. In some embodiments of the present inventive concept, timing and synchronization of imaging acquisition may be, for example, 1.0 seconds for $SpO_2$, 8.0 seconds for MSPV, and 1 second for $SpO_2$, since simultaneous illumination will change the imaging data. The LED illumination microcontroller device may be programmed and incorporated into the MSPV hardware/software in some embodiments.

Figure 24:
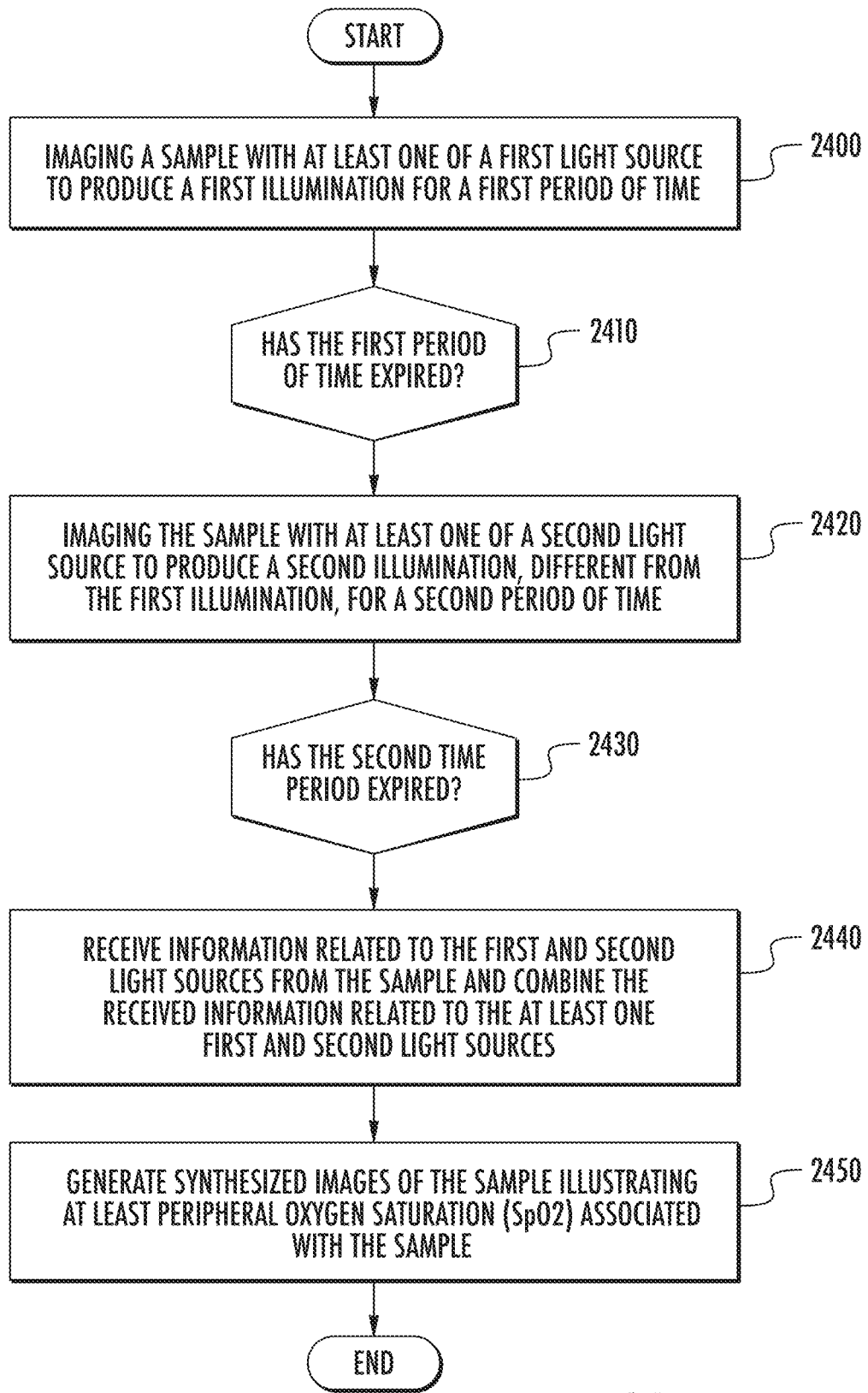
FIG. 24 is a flowchart illustrating operations in accordance with some embodiments of the present inventive concept.

Referring now to FIG. 24, a flowchart illustrating operations in accordance with some embodiments of the present inventive concept will be discussed. As illustrated in FIG. 24, operations for obtaining a multispectral imaging system begin at block 2400 by imaging a sample with a least one first light source having at least one first wavelength configured to produce a first illumination for a first period of time. In some embodiments, the at least one first light source may be two light sources, a first configured to image a surface of the sample and the second configured to penetrate that sample and provide information from the penetrated depth. These two light sources may illuminate the sample for a first period of time, for example, about 8 seconds. It will be determined if the first period of time has expired (block 2410). If the first period of time has not expired (block 2410), operations continue at block 2400 so that at least one first light source continues to illuminate the sample. If, on the other hand, the first period of time has expired (block 2410), the at least one first light source is turned off and the sample is imaged using at least one second light source for a second period of time, which is different from the first period of time (2420). For example, the second period of time may be about 1.0 seconds in some embodiments. It will be understood that in some embodiments, the at least first and second light sources are not turned on at the same time. These light sources provide illuminate for different purposed and may interfere with one another if they are turned on at the same time.

It is determined if the second period of time has expired (block 2430). If the second period of time has not expired (block 2430), operations continue at block 2420 and the at least one second light source continues to illuminate the sample. If, on the other hand, it is determined that the second time period has expired (block 2430), information related to the at least one first and second light sources are received from the sample and combined (block 2440). Synthesized images of the sample are generated illustrating at least peripheral oxygen saturation ($SpO_2$) associated with the sample. Thus, in some embodiments a first set of wavelengths may be used to illuminate the sample to obtain MSPV data and a second set of wavelengths may be used to illuminate the sample to obtain other data including $SpO_2$ data. As discussed, these wavelengths may illuminate the sample at different times so as to provide the most accurate output.

In some embodiments, the one of the light sources may have a wavelength in a red spectrum from 700 nm to 800 nm, which is used to determine peripheral oxygen saturation ($SpO_2$). In other embodiments, the SpO2 data may be provided by first and second light emitting diodes (LEDs) without departing from the scope of the present inventive concept.

As briefly discussed above, by combining MPSV+$SpO_2$ (both non-invasively determined through our core technology plus modifications) and having an index of anemia, all three components of what can generate hypoxia at the tissue level are known (not DIAGNOSTIC of hypoxia, but much more useful in hypoxia circumstances than $SpO_2$ alone). Obtaining all three of these parameters simultaneously is novel above and beyond obtaining $SpO_2$ through our novel approach by itself. This combination may provide new and important insight into differences between hypoxemic and hypoxic conditions.

In the drawings and specification, there have been disclosed example embodiments of the inventive concept. Although specific terms are employed, they are used in a generic and descriptive sense only and not for purposes of limitation, the scope of the inventive concept being defined by the following claims.

That which is claimed is:

1. A multispectral imaging system, the system comprising:
   a first laser light source having a first wavelength configured to produce a non-coherent illumination to image a sample;
   a second coherent laser light source, different from the first laser light source, having a second wavelength, different from the first wavelength, configured to image the sample simultaneously with the first laser light source;
   a single multi-sensor camera configured to simultaneously receive information related to the first and second laser light sources from the sample, wherein light at the first wavelength is configured to image a surface of the sample into the camera and light at the second wavelength is configured to penetrate the sample and provide information related to the penetrated sample to the camera; and
   a processor configured to combine the received information related to the first and second laser light sources and generate synthesized images of the sample illustrating peripheral oxygen saturation ($SpO_2$) associated with the sample in real-time,
   wherein the synthesized images of the sample illustrating $SpO_2$ generated in real-time are generated within several milliseconds so as to appear as if the data was provided immediately upon request or activation of first and second laser light sources.

2. The system of claim 1, wherein the first laser light source is one of coherent, non-coherent and partially coherent.

3. The system of claim 1, further comprises:
   at least one additional light source, different from the first and second laser light source, the at least one additional light source having a third wavelength, different from the first or second wavelengths, configured to image the sample in conjunction or simultaneously with the first and second laser light sources,
   wherein the processor is further configured to combine the received information related to the first, second and at least one additional light sources and generate synthesized images of the sample illustrating blood flow distribution and peripheral oxygen saturation ($SpO_2$) associated with the sample.

4. The system of claim 3, wherein at least one of the first, second and at least third light sources are periodically switched on and/or off to allow remaining ones of the first, second and at least third light sources to image the sample.

5. The system of claim 3 wherein the first and second laser light sources are turned on for a period of about 8 seconds and wherein at least one third light source is turned on for about 1 second, such that the first and second laser light sources are not turned on while the at least one third light source is turned on.

6. The system of claim 4, wherein at least one of the first, second and at least third light sources has a wavelength in a red spectrum from 700 nm to 800 nm and wherein the wavelength in the red spectrum is configured to determine peripheral oxygen saturation ($SpO_2$).

7. The system of claim 4, wherein the at least one third light source comprises first and second light emitting diodes (LEDs) configured to image the same and provide data to determine peripheral oxygen saturation ($SpO_2$).

8. A multispectral imaging system, the system comprising:
   a first laser light source having a first wavelength configured to produce a non-coherent illumination to image a sample;
   a second coherent laser light source, different from the first laser light source, having a second wavelength, different from the first wavelength, configured to image the sample simultaneously with the first laser light source, the first and second wavelengths being configured to provide information from the sample at different depths of the sample;
   at least one third light source, different from the first and second laser light sources and having at least one third wavelength, wherein the at least one third wavelength is configured to provide different information from the sample than the first and second wavelengths;
   a single multi-sensor camera configured to receive information related to the first and second laser light sources from the sample during a first time period and the different information related to the at least one third wavelength from the sample during a second time period, different from the first time period; and
   a processor configured to combine the received information related to the first, second and at least one third laser light sources and generate synthesized images of the sample and quantify peripheral oxygen saturation ($SpO_2$) associated with the sample in real-time,.
   wherein the synthesized images of the sample and quantification of $SpO_2$ generated in real-time are generated within several milliseconds so as to appear as if the data was provided immediately upon request or activation of first, second and at least one third laser light sources.

9. The system of claim 8, wherein light at the first wavelength is configured to image a surface of the sample into the camera and light at the second wavelength is configured to penetrate the sample and provide information related to the penetrated sample to the camera.

10. The system of claim 9, wherein the first laser light source is one of coherent, non-coherent and partially coherent.

11. The system of claim 10, wherein the first and second laser light source are turned on during the first time periods and off during the second time period and wherein the at least one third light source is turned off during the first time period and turned on during the second time period.

12. The system of claim 11, wherein the first time period is about 8 seconds and wherein the second time period is about 1.0 second.

13. The system of claim 12, wherein the at least one third light source has a wavelength in a red spectrum from 700 nm to 800 nm and wherein the wavelength in a red spectrum is configured to determine at least a peripheral oxygen saturation ($SpO_2$) level in the sample.

14. The system of claim 12, wherein the at least one third light source comprises first and second light emitting diodes (LEDs) configured to image the same and provide data to determine a peripheral oxygen saturation ($SpO_2$) in the sample.

15. A method for obtaining a multispectral imaging system, the method comprising:
   imaging a sample with at least one first laser light source having at least one first wavelength configured to produce a first illumination for a first period of time;
   imaging the sample with at least one second light source, different from the at least one first laser light source, having at least one second wavelength, different from the at least one first wavelength, for a second period of time, wherein the first and second period of time do not overlap;
   receiving information related to the at least one first laser light source and second light source from the sample at a single multi-sensor camera; and
   combining the received information related to the at least one first laser light and second light source; and
   generating synthesized images of the sample illustrating at least peripheral oxygen saturation ($SpO_2$) associated with the sample in real time,
   wherein generating the synthesized images of the sample illustrating $SpO_2$ in real-time comprises generating the synthesized images of the sample illustrating $SpO_2$ are generated within several milliseconds so as to appear as if the data was provided immediately upon request or activation of first and second laser light sources.

16. The method of claim 15, wherein the at least one first laser light source and second light source are periodically switched on and/or off to allow remaining light sources to image the sample.

17. The method of claim 16 wherein the at least one first laser light source is turned on for a period of about 8 seconds and wherein the at least one second light source is turned on for about 1 second, such that at least one first laser light source and second light source are not turned at the same time.

18. The method of claim 16, wherein at least one of the at least first laser light source and second light source has a wavelength in a red spectrum from 700 nm to 800 nm and wherein the wavelength in the red spectrum is configured to determine a level of peripheral oxygen saturation ($SpO_2$) in the sample.

19. The method of claim 16, wherein the at least one second light source comprises first and second light emitting diodes (LEDs) configured to image the same and provide data to determine a level of peripheral oxygen saturation ($SpO_2$) in the sample.

* * * * *

UNITED STATES PATENT AND TRADEMARK OFFICE
CERTIFICATE OF CORRECTION

PATENT NO. : 11,278,220 B2
APPLICATION NO. : 16/433716
DATED : March 22, 2022
INVENTOR(S) : Tucker et al.

Page 1 of 2

It is certified that error appears in the above-identified patent and that said Letters Patent is hereby corrected as shown below:

On the Title Page

(56) References Cited, US Patent Documents, p. 2, left column:
Please correct "20180234603 08-2018 Moore" to read -- 20180234603 08-2018 Moore et al. --

Other Publications, p. 2, left column, Bornstein cite:
Please correct "eye vs: SPY" to read -- eye vs. SPY --

Other Publications, p. 2, right column, Criqui cite:
Please correct "Aboyars V." to read -- Aboyans V. --

Other Publications, p. 2, right column, De Bruyne cite:
Please correct "Jagie N" to read -- Jagic N --

Other Publications, p. 2, right column, 2nd Ferguson cite:
Please correct "blood fow in" to read -- blood flow in --

Other Publications, p. 2, right column, 2nd Fowkes cite:
Please correct "1329-4340" to read -- 1329-1340 --

Other Publications, p. 3, left column, 1st McDermott cite:
Please correct "Criqul MH" to read -- Criqui MH --

Other Publications, p. 3, right column, Vaz cite:
Please correct "IEEE Rev Blomed" to read -- IEEE Rev Biomed --

In the Specification

Column 12, Line 2:
Please correct "wavelength; Δf is" to read -- wavelength; $\Delta f$ is --

Signed and Sealed this
Twenty-sixth Day of April, 2022

Katherine Kelly Vidal
*Director of the United States Patent and Trademark Office*

CERTIFICATE OF CORRECTION (continued)

Column 15, Line 33:
Please correct "from 0-1" to read -- from 0~1 --

Column 17, Equation (5):
Please correct "$R(x,y) = (2^N - 1) \times a_1 \times \left(\frac{NIR(x,y) - \min(NIR(x,y))}{\max(NIR(x,y)) - \min(NIR(x,y))}\right)^{b_1}$" to read -- $R(x,y) = (2^N - 1) \times a_1 \times \left(\frac{NIR(x,y) - \min(NIR(x,y))}{\max(NIR(x,y)) - \min(NIR(x,y))}\right)^{b_1}$ --

Column 17, Equation (6):
Please correct "$G(x,y) = (2^N - 1) \times a_2 \times \left(\frac{VIS(x,y) - \min(VIS(x,y))}{\max(VIS(x,y)) - \min(VIS(x,y))}\right)^{b_2}$" to read -- $G(x,y) = (2^N - 1) \times a_1 \times \left(\frac{VIS(x,y) - \min(VIS(x,y))}{\max(VIS(x,y)) - \min(VIS(x,y))}\right)^{b_2}$ --

Column 17, Equation (7):
Please correct "$B(x,y) = (2^N - 1) \times a_3 \times \left(\frac{VIS(x,y) - \min(VIS(x,y))}{\max(VIS(x,y)) - \min(VIS(x,y))}\right)^{b_3}$" to read -- $B(x,y) = (2^N - 1) \times a_3 \times \left(\frac{VIS(x,y) - \min(VIS(x,y))}{\max(VIS(x,y)) - \min(VIS(x,y))}\right)^{b_3}$ --

Column 17, Equation (8):
Please correct "$\frac{NIR(x,y) - \min(NIR(x,y))}{\max(NIR(x,y)) - \min(NIR(x,y))}$" to read -- $\frac{NIR(x,y) - \min(NIR(x,y))}{\max(NIR(x,y)) - \min(NIR(x,y))}$ --